US011272853B2

United States Patent
Nishikawa et al.

(10) Patent No.: US 11,272,853 B2
(45) Date of Patent: Mar. 15, 2022

(54) BAG-SHAPED STRUCTURE USED IN A CUFF FOR BLOOD PRESSURE MEASUREMENT

(71) Applicants: OMRON CORPORATION, Kyoto (JP); OMRON HEALTHCARE CO., LTD., Muko (JP)

(72) Inventors: Kazuyoshi Nishikawa, Ritto (JP); Shuhei Ojiro, Kyoto (JP); Tomoyuki Nishida, Takatsuki (JP)

(73) Assignees: OMRON CORPORATION; OMRON HEALTHCARE CO., LTD.

( * ) Notice: Subject to any disclaimer, the term of this patent is extended or adjusted under 35 U.S.C. 154(b) by 35 days.

(21) Appl. No.: 16/468,450

(22) PCT Filed: Dec. 26, 2017

(86) PCT No.: PCT/JP2017/046653
§ 371 (c)(1),
(2) Date: Jun. 11, 2019

(87) PCT Pub. No.: WO2018/146968
PCT Pub. Date: Aug. 16, 2018

(65) Prior Publication Data
US 2020/0187799 A1  Jun. 18, 2020

(30) Foreign Application Priority Data
Feb. 13, 2017 (JP) .................. 2017-024244

(51) Int. Cl.
*A61B 5/02* (2006.01)
*A61B 5/022* (2006.01)
(Continued)

(52) U.S. Cl.
CPC ...... *A61B 5/02233* (2013.01); *A61B 5/02141* (2013.01); *A61B 5/7445* (2013.01)

(58) Field of Classification Search
CPC ... A61B 5/02233; A61B 5/7445; A61B 5/022; A61B 5/021; A61B 5/02141;
(Continued)

(56) References Cited

U.S. PATENT DOCUMENTS 3,760,795 A * 9/1973 Adelhed ............ A61B 5/02233
600/499
4,637,394 A * 1/1987 Racz .................... A61B 17/135
606/202

(Continued)

FOREIGN PATENT DOCUMENTS

| CN | 1308918 A | 8/2001 |
| CN | 2595322 Y | 12/2003 |

(Continued)

OTHER PUBLICATIONS

English-language machine translation of JP-2002224056-A (Year: 2021).*
(Continued)

*Primary Examiner* — Andrey Shostak
(74) *Attorney, Agent, or Firm* — Harness, Dickey & Pierce, P.L.C.

(57) ABSTRACT

To provide a bag-shaped structure that can suppress expansion of the side wall portion and improve the vascular compression property. A bag-shaped structure used in a cuff for a blood pressure monitor configured to be wrapped around a living body, inflate when a fluid is supplied to an internal space, and compress the living body includes: an inner wall portion provided on a living body side; an outer wall portion facing the inner wall portion; and a pair of side wall portions continuous with the inner wall portion and the outer wall portion and including a bent portion bent toward the internal space; and a reinforcing member provided on each of the pair of side wall portions, having a higher hardness than the side wall portion, and having shape
(Continued)

followability in a direction of wrapping around the living body.

7 Claims, 16 Drawing Sheets

(51) Int. Cl.
*A61B 5/00* (2006.01)
*A61B 5/021* (2006.01)

(58) Field of Classification Search
CPC .......... A61B 5/6824; A61B 5/681; A61B 5/02; A61B 8/04; A61B 17/135; A61B 5/34; A61F 5/34
See application file for complete search history.

(56) References Cited

U.S. PATENT DOCUMENTS

| | | | |
|---|---|---|---|
| 6,527,727 | B2 | 3/2003 | Itonaga et al. |
| 6,758,821 | B2 | 7/2004 | Itonaga et al. |
| 6,866,636 | B2 | 3/2005 | Inoue et al. |
| 7,794,405 | B2 | 9/2010 | Karo et al. |
| 2001/0016692 | A1* | 8/2001 | Itonaga ............ A61B 5/02233 600/499 |
| 2003/0055347 | A1 | 3/2003 | Itonaga et al. |
| 2004/0034308 | A1 | 2/2004 | Inoue et al. |
| 2006/0135873 | A1* | 6/2006 | Karo ................ A61B 5/02233 600/499 |
| 2006/0178584 | A1 | 8/2006 | Karo et al. |
| 2006/0184054 | A1 | 8/2006 | Sano et al. |
| 2010/0004676 | A1* | 1/2010 | McEwen ............ A61B 17/1322 606/202 |
| 2015/0088011 | A1* | 3/2015 | Taniguchi .......... A61B 5/02233 600/499 |
| 2018/0153418 | A1 | 6/2018 | Sullivan et al. |
| 2019/0261870 | A1 | 8/2019 | Nishikawa |
| 2020/0187798 | A1 | 6/2020 | Nishikawa et al. |
| 2020/0187799 | A1 | 6/2020 | Nishikawa et al. |

FOREIGN PATENT DOCUMENTS

| | | | | |
|---|---|---|---|---|
| CN | 1470217 | A | | 1/2004 |
| CN | 1792320 | A | | 6/2006 |
| CN | 1813626 | A | | 8/2006 |
| CN | 1820702 | A | | 8/2006 |
| CN | 104394761 | A | | 3/2015 |
| CN | 104811517 | A | | 7/2015 |
| JP | S56076933 | A | | 6/1981 |
| JP | S61-037135 | A | | 2/1986 |
| JP | H09117419 | A | | 5/1997 |
| JP | 2001224558 | A | | 8/2001 |
| JP | 2002224056 | A | * | 8/2002 |
| JP | 2003144398 | A | | 5/2003 |
| JP | 2003325462 | A | | 11/2003 |
| JP | 2004016566 | A | | 1/2004 |
| JP | 2006174860 | A | | 7/2006 |
| JP | 2006-218178 | A | | 8/2006 |
| JP | 3168377 | U | | 6/2011 |
| JP | 2012075780 | A | | 4/2012 |
| JP | 2013031545 | A | | 2/2013 |
| WO | WO-2016205549 | A1 | * | 12/2016 ......... A61B 5/02233 |
| WO | 2017017991 | A1 | | 2/2017 |

OTHER PUBLICATIONS

U.S. Appl. No. 16/348,978, filed May 10, 2019, Nishikawa.
U.S. Appl. No. 16/348,988, filed May 10, 2019, Nishikawa et al.
U.S. Appl. No. 16/349,034, filed May 10, 2019, Nishikawa.
U.S. Appl. No. 16/349,083, filed May 10, 2019, Ojiro et al.
U.S. Appl. No. 16/468,361, filed Jun. 11, 2019, Nishikawa et al.
U.S. Appl. No. 16/468,395, filed Jun. 11, 2019, Nishikawa et al.
Japanese Office Action dated Aug. 11, 2020 (with English translation) for Japanese Patent Application No. 2017-024244 (5 pages).
International Search Report (in English and Japanese) and Written Opinion (in Japanese) issued in PCT/JP2017/046653, dated Mar. 20, 2018; ISA/JP.
International Preliminary Report on Patentability for International Application No. PCT/JP2017/046653, dated Aug. 13, 2019.
Chinese Office Action dated May 11, 2021 for Application No. 201780076304.8 with English translation (18 pages).
International Search Report (in English and Japanese) and Written Opinion (in English and Japanese) issued in PCT/JP2017/046646, dated Feb. 27, 2018; ISA/JP.
International Preliminary Report on Patentability for International Application No. PCT/JP2017/046646, dated Jul. 11, 2019, (7 pages).
Japanese Office Action dated Sep. 29, 2020 (with English translation) for Japanese Patent Application No. 2016-254274 (12 pages).
Japanese Office Action dated Mar. 30, 2021 for Japanese Patent Application No. 2016-254274 with English translation (5 pages).
First Chinese Office Action for corresponding Application No. 201780068495.3 dated Apr. 20, 2021 with English translation (17 Pages).
International Search Report (in English and Japanese) and Written Opinion (in Japanese) issued in PCT/JP2017/046648, dated Feb. 6, 2018; ISA/JP.
International Preliminary Report on Patentability for International Application No. PCT/JP2017/046648, dated Aug. 13, 2019, (6 pages).
Office Action regarding Chinese Patent Application No. 201780076346.1, dated May 21, 2021.
Chinese Office Action dated Oct. 9, 2021 (with English Translation) for Chinese Application No. 201780076304.8 (11 pages).
Chinese Office Action for Chinese Application No. 201780068495.3 (with English Translation) dated Nov. 18, 2021 (13 pages).

* cited by examiner

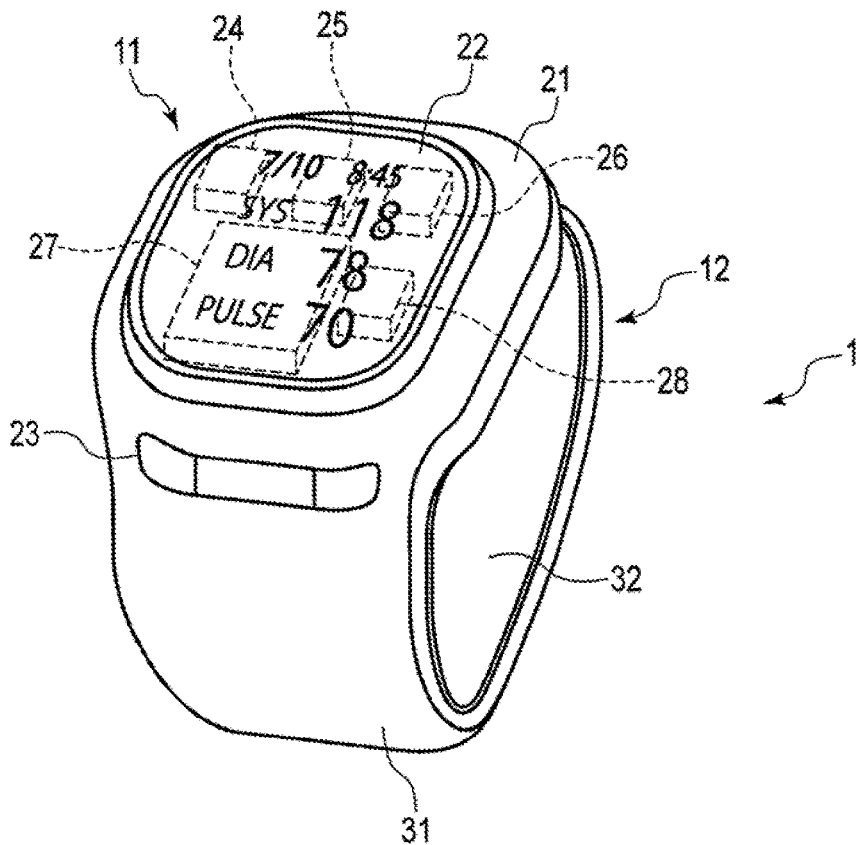
F I G. 1
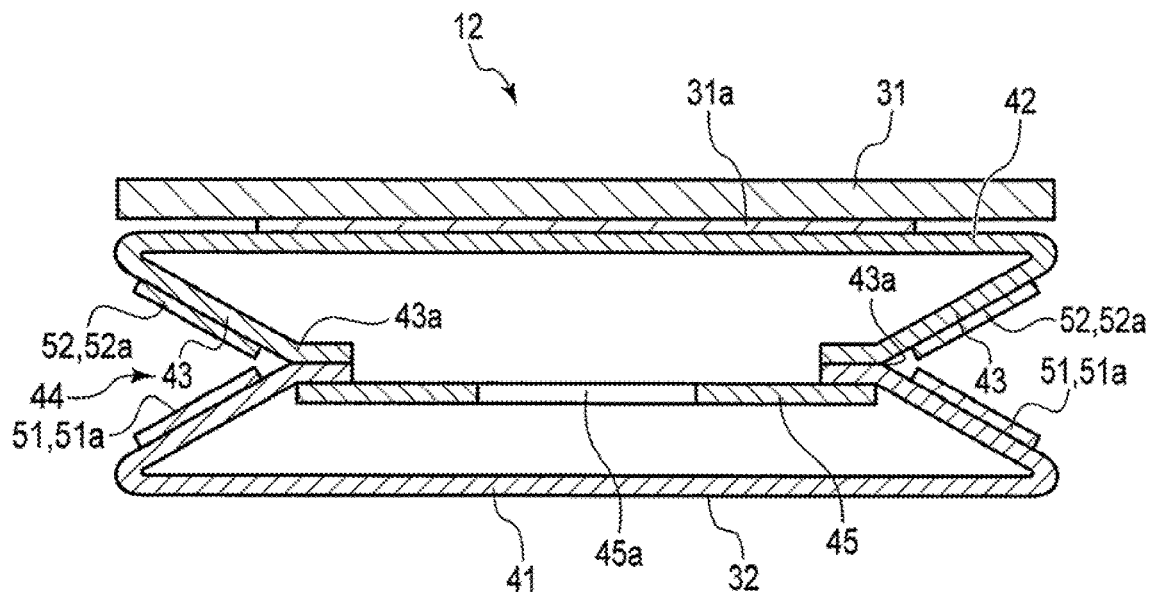
F I G. 2

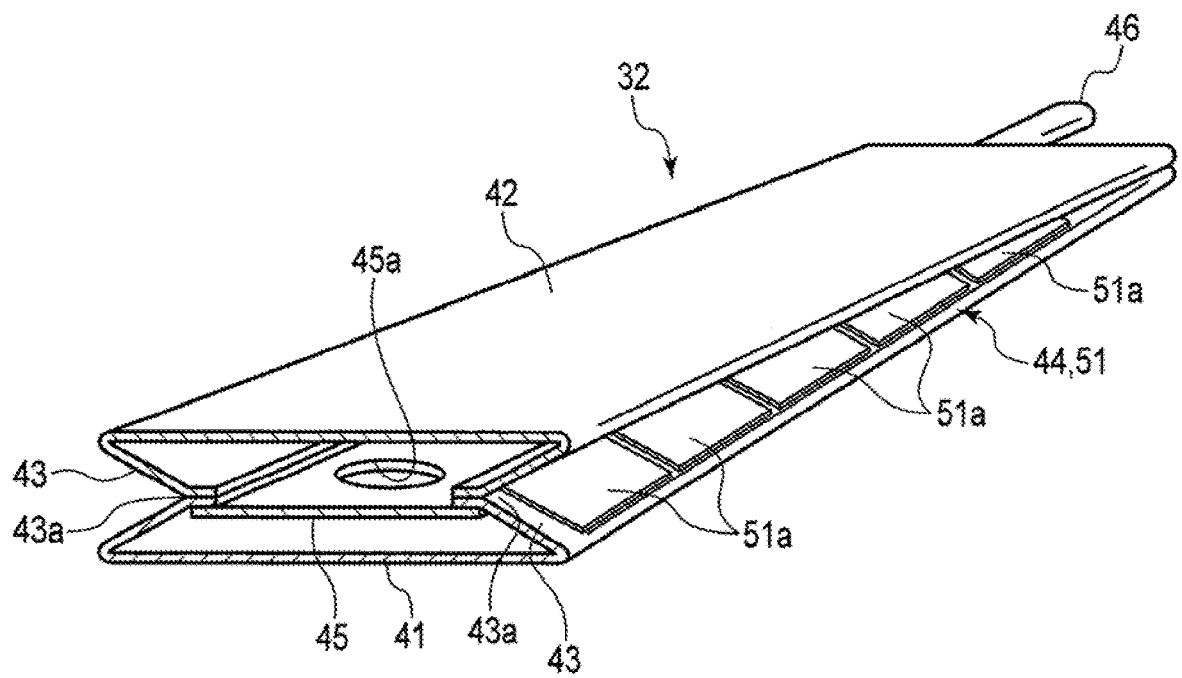
F I G. 5
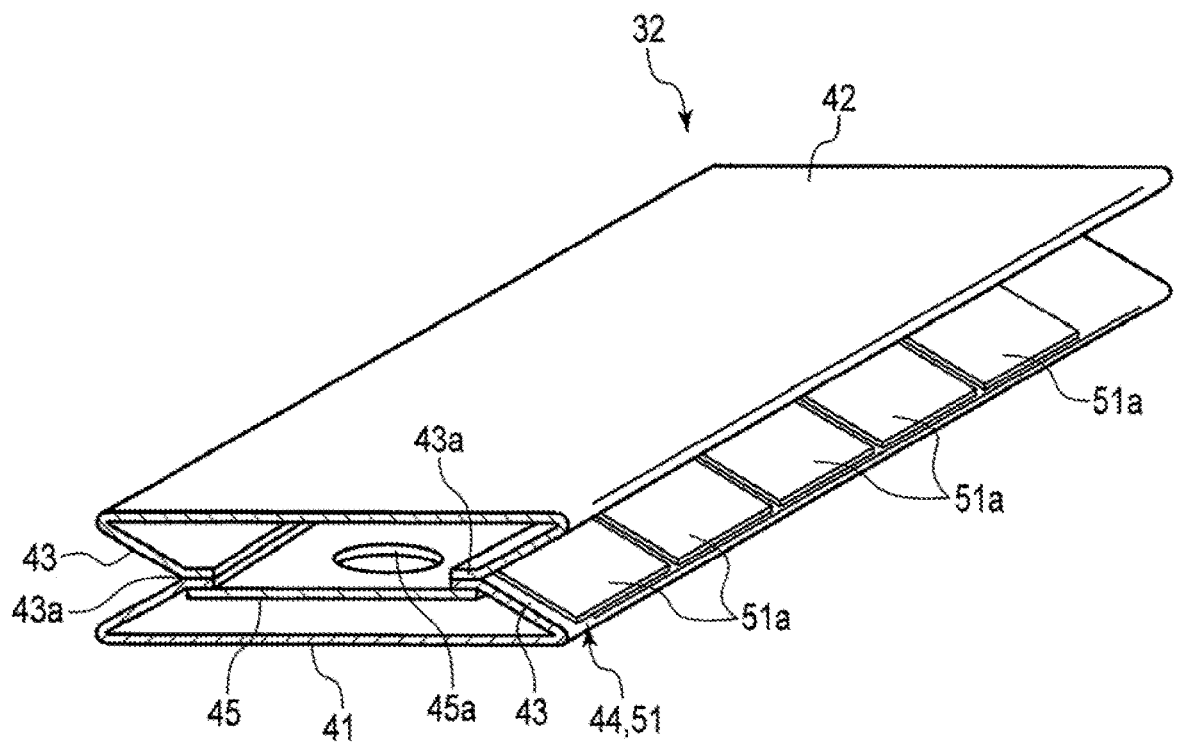
F I G. 6

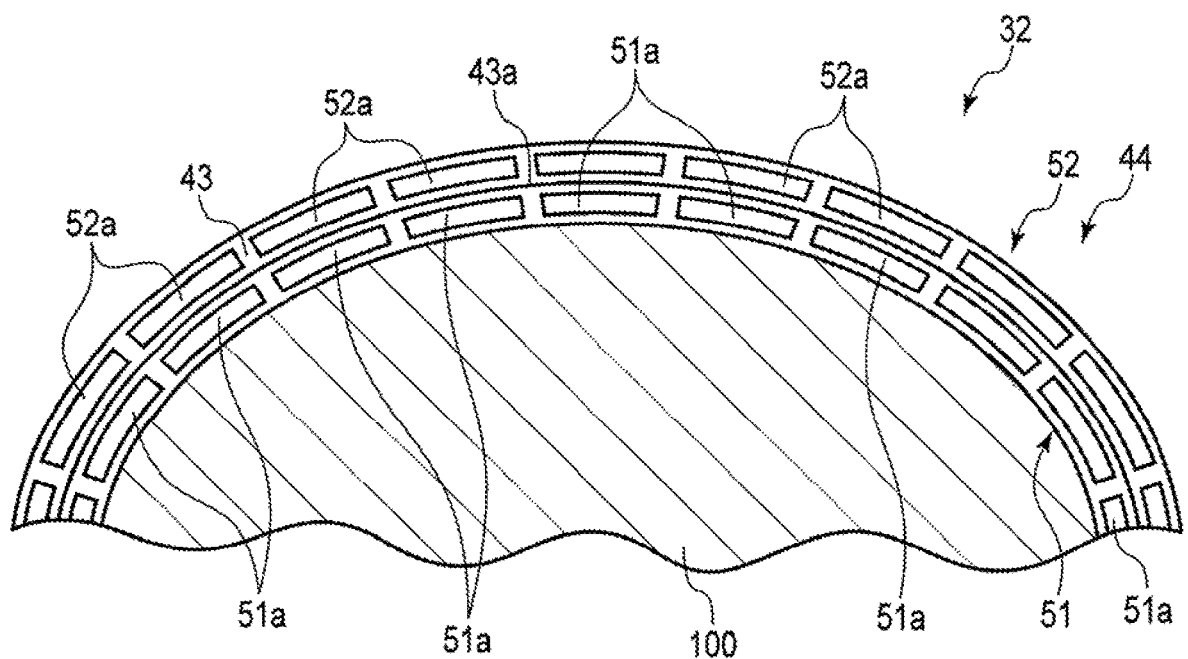
F I G. 7

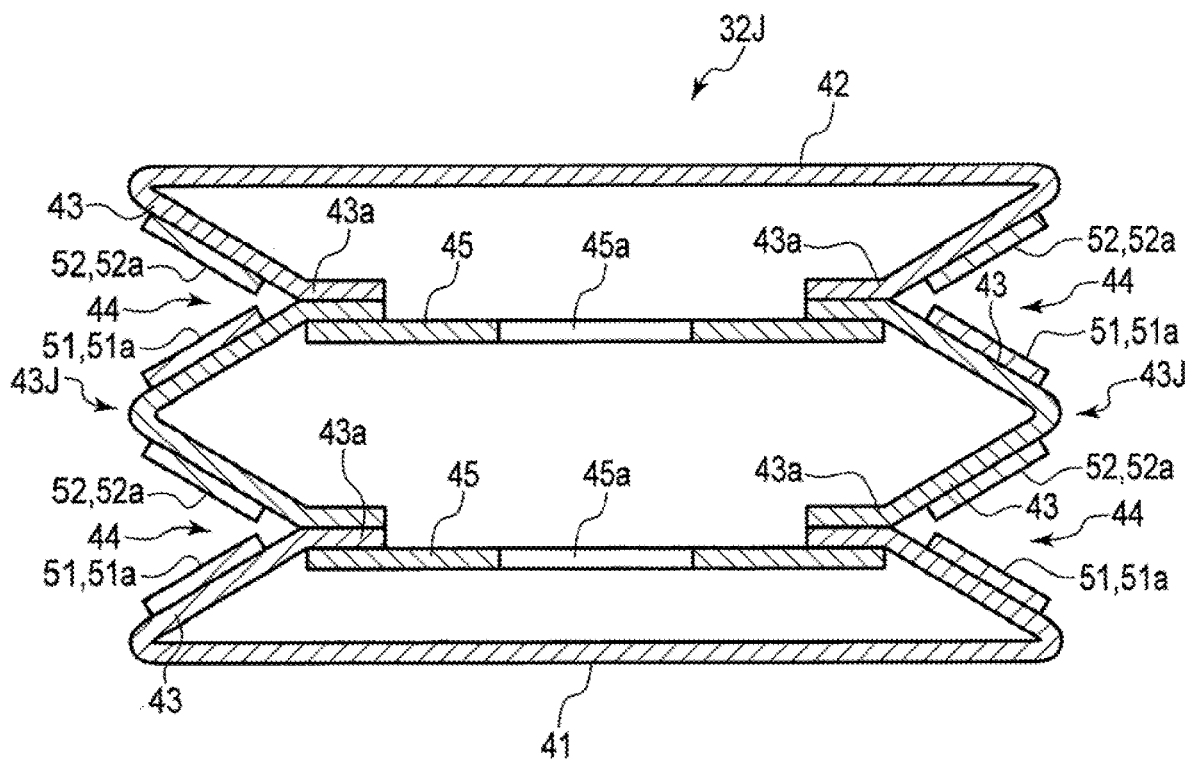
F I G. 18
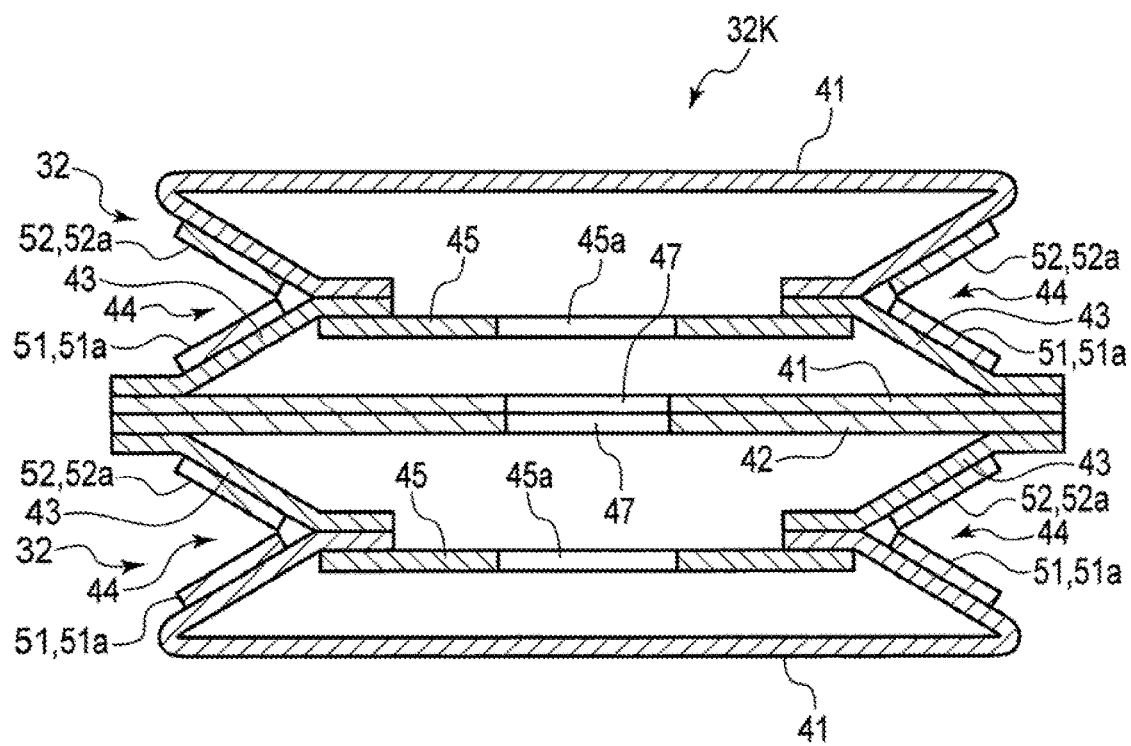
F I G. 19

BAG-SHAPED STRUCTURE USED IN A CUFF FOR BLOOD PRESSURE MEASUREMENT

CROSS-REFERENCE TO RELATED APPLICATIONS

This is a U.S. National Phase Application under 35 U.S.C. 371 of International Application No. PCT/JP2017/046653 (not published in English), filed Dec. 26, 2017, which claims priority to Japanese Patent Application No. 2017-024244, filed Feb. 13, 2017. The disclosures of the above applications are incorporated herein by reference.

FIELD

The present invention relates to a bag-shaped structure that compresses a living body in blood pressure measurement.

BACKGROUND

In recent years, a blood pressure monitor used for blood pressure measurement is utilized not only in medical facilities, but also in households as means for checking health conditions. A blood pressure monitor measures a blood pressure by wrapping a cuff including a bag-shaped structure around an upper arm or a wrist, etc. of a human body and by inflating and deflating the bag-shaped structure to detect a pulse generated in an artery and vibrations of an arterial wall. Regarding such a blood pressure monitor, there is demand for size reduction to enhance portability and usability. To reduce the size of the cuff, reduction in the cuff width of a bag-shaped structure used in the cuff is required. However, reduction in the cuff width of the bag-shaped structure reduces the vascular compression area, and increases the dispersion in pulse wave measurements, which causes the problem that precise blood pressure measurement becomes difficult.

A bag-shaped structure having a so-called Σ structure or bellows structure, in which a pair of side wall portions including bent portions bent toward the internal space are provided between an inner wall portion provided on the living body side and an outer wall portion facing the inner wall portion, is known (see, for example, Jpn. Pat. Appln. KOKAI Publication No. 2003-325462). The bag-shaped structure having such a configuration is specialized in inflating toward the living body and compressing the living body. In addition to the bellows structure, a configuration in which the thickness of the inner wall portion is reduced and a configuration in which a flexible material is used are under consideration in order to further improve the vascular compression property. A technique of causing the inner wall portion to follow the wrist shape or the like of the living body by the inflation pressure of the bag-shaped structure as described above is known.

SUMMARY

However, if a common bag-shaped structure with a bellows structure has a configuration in which the thickness of side wall portions is reduced or a configuration in which the side wall portions are made of a flexible material, the side wall portions are expanded outward by the inflation pressure when the bag-shaped structure is inflated. Since the inflation pressure is lost at the expanded portions, the bag-like structure with the bellows structure may cause variation in compression pressure for compressing the living body when the bag-shaped structure is inflated and compresses the living body. Accordingly, if a bag-shaped structure with a bellows structure is used in the cuff, the expansion of the side wall portions may cause dispersion in pulse wave measurements.

Therefore, the present invention is intended to provide a bag-shaped structure which can achieve high blood pressure measurement accuracy even when the cuff width is reduced.

A first aspect of the present invention provides a bag-shaped structure used in a cuff for blood pressure measurement configured to be wrapped around a living body, inflate when a fluid is supplied to an internal space, and compress the living body, the bag-shaped structure comprising: an inner wall portion provided on a living body side; an outer wall portion facing the inner wall portion; a pair of side wall portions, each being continuous with the inner wall portion and the outer wall portion and including a bent portion bent toward the internal space; and a reinforcing member provided on each of the pair of side wall portions, having a higher hardness than the side wall portion, and having shape followability in a direction of wrapping around the living body.

The shape followability is a property that enables the bag-shaped structure provided with the reinforcing member to change in shape in accordance with the shape of the contact portion of the wrist, etc. of the living body when wrapped around the living body. Namely, the reinforcing member having shape followability means a reinforcing member capable of, when provided in the bag-shaped structure, providing the bag-shaped structure with a property to roughly follow the shape of the contact portion of the living body. Therefore, the reinforcing member having shape followability does not need to have a property that enables the reinforcing member itself to change in shape so that the bag-shaped structure follows the shape of the contact portion of the living body to such an extent that the surface of the inner wall portion of the bag-shaped structure, which comes into contact with the living body, comes into close contact with the living body.

A second aspect of the present invention provides the bag-shaped structure according to the first aspect, wherein the reinforcing member is provided on the side wall portion on each of the inner wall portion side and the outer wall portion side with respect to the bent portion.

A third aspect of the present invention provides the bag-shaped structure according to the second aspect, wherein the reinforcing member includes a plurality of plate-shaped small pieces provided at predetermined intervals in a longitudinal direction of the side wall portion.

A fourth aspect of the present invention provides the bag-shaped structure according to the third aspect, wherein, of the small pieces, small pieces provided on the inner wall portion side on the side wall portion are shorter in the longitudinal direction of the side wall portion than small pieces provided on the outer wall portion side on the side wall portion.

A fifth aspect of the present invention provides the bag-shaped structure according to the third aspect, wherein the small pieces are integrally connected on the inner wall portion side.

A sixth aspect of the present invention provides the bag-shaped structure according to the second aspect, wherein the reinforcing member is provided along the longitudinal direction of the side wall portion and is meshed.

A seventh aspect of the present invention provides the bag-shaped structure according to the sixth aspect, wherein at least the reinforcing member provided on the inner wall portion side of the side wall portion includes a plurality of small pieces provided at predetermined intervals in the longitudinal direction of the side wall portion.

An eighth aspect of the present invention provides the bag-shaped structure according to the first aspect, wherein the bag-shaped structure comprises a plurality of the reinforcing members, the reinforcing members being provided at predetermined intervals in a longitudinal direction of the side wall portion and each including a perforation on the bent portion along the bent portion.

A ninth aspect of the present invention provides the bag-shaped structure according to the first aspect, wherein the reinforcing member is provided on an outer surface of the side wall portion.

A tenth aspect of the present invention provides the bag-shaped structure according to the first aspect, wherein the reinforcing member is provided inside the side wall portion.

An eleventh aspect of the present invention provides the bag-shaped structure according to the first aspect, wherein the inner wall portion and the side wall portion have a Shore A hardness in a range from 15 to 95.

According to the first aspect, on the side wall portion of the bag-shaped structure, a reinforcing member having a higher hardness than the side wall portion and having shape followability in a direction of wrapping around the living body is provided; therefore, expansion of the side wall portion can be suppressed, and the vascular compression property can be improved. As a result, even when the cuff width is reduced, the bag-shaped structure can attain high blood pressure measurement accuracy.

According to the second aspect, the reinforcing member is provided on the inner wall portion side and the outer wall portion side of the side wall portion with respect to the bent portion; therefore, inflation and deflation of the bag-shaped structure can be prevented from being inhibited.

According to the third aspect, the side wall portion can be bent between a plurality of small pieces; therefore high shape followability can be attained.

According to the fourth aspect, the small pieces on the inner wall portion side are shorter in the longitudinal direction of the side wall portion than the small pieces on the outer wall portion side; therefore, high shape followability can be given to the inner wall portion side with a smaller curvature radius when the bag-shaped structure is wrapped around the living body.

According to the fifth aspect, since a plurality of small pieces are integrally connected on the inner wall portion side, the reinforcing member can be easily fixed to the side wall portion, and since they are connected on the side wall portion side with a smaller curvature radius, shape followability can be prevented from being lowered.

According to the sixth aspect, the reinforcing member is provided along the longitudinal direction of the side wall portion and is meshed, and thus has high flexibility; therefore, shape followability can be prevented from being lowered.

According to the seventh aspect, at least the reinforcing member provided on the inner wall portion side of the side wall portion is comprised of a plurality of small mesh pieces; therefore, high shape followability can be attained by the division as well as the flexibility provided by the mesh.

According to the eighth aspect, a plurality of reinforcing members are provided at predetermined intervals in the longitudinal direction of the side wall portion, and each reinforcing member has a perforation on the bent portion of the side wall portion along the bent portion; therefore, inflation and deflation of the bag-shaped structure are not inhibited and the number of small pieces can be reduced, which makes manufacturing easier.

According to the ninth aspect, the reinforcing member is provided on the outer surface of the side wall portion; therefore, the reinforcing member can be fixed after the sheet member is manufactured.

According to the tenth aspect, the reinforcing member is provided inside the side wall portion; therefore, the reinforcing member can be provided when the sheet member is manufactured.

According to the eleventh aspect, even when the inner wall portion and side wall portion are soft and have a Shore A hardness in the range from 15 to 95, the reinforcing member can prevent expansion of the side wall portion.

BRIEF DESCRIPTION OF THE DRAWINGS

FIG. 1 is a perspective view showing a configuration of a blood pressure monitor according to one embodiment of the present invention.

FIG. 2 is a cross-sectional view showing a configuration of a cuff used in the blood pressure monitor.

FIG. 5 is a partially cutaway perspective view showing a configuration of a bag-shaped structure used in the cuff.

FIG. 6 is a partially cutaway perspective view showing the configuration of the bag-shaped structure used in the cuff.

FIG. 7 is a side view schematically showing the configuration of the bag-shaped structure in the state of being wrapped around the living body, in a direction orthogonal to the wrapping direction.

FIG. 18 is a cross-sectional view showing a configuration of a bag-shaped structure according to a tenth modification of the present invention.

FIG. 19 is a cross-sectional view showing a configuration of a bag-shaped structure according to an eleventh modification of the present invention.

DETAILED DESCRIPTION

Embodiment

Hereinafter, a blood pressure monitor 1 including a cuff 12 using a bag-shaped structure 32 according to one embodiment of the present invention will be described with reference to FIGS. 1 to 8.

Figure 3:
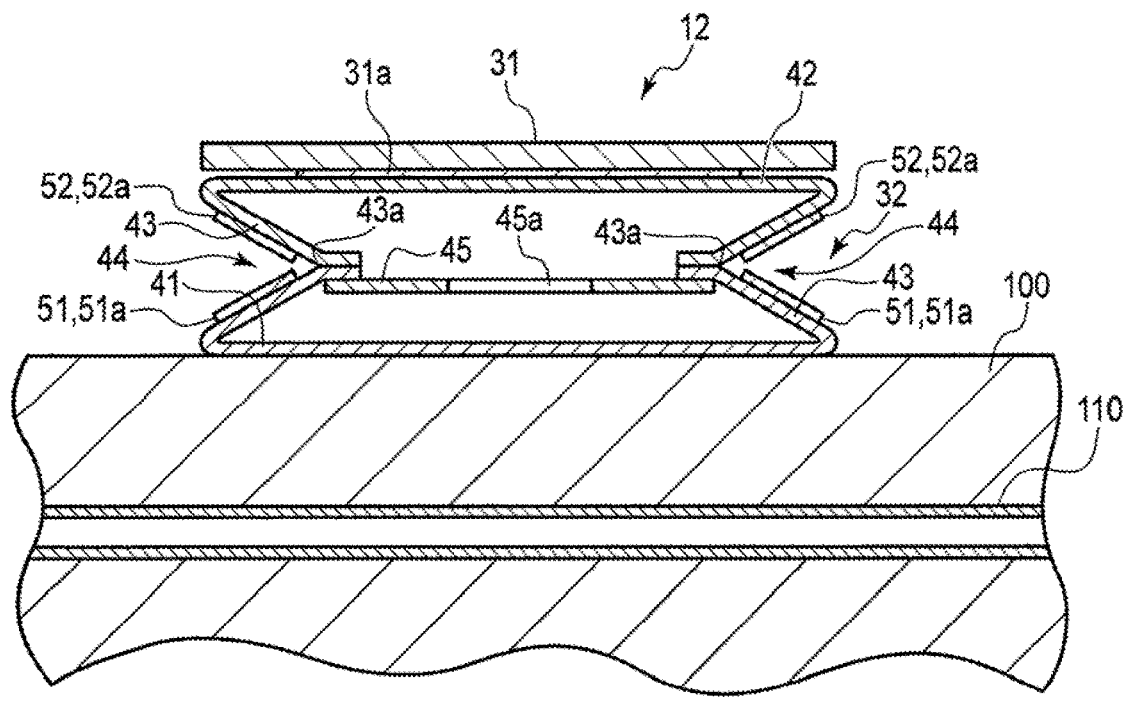
FIG. 3 is a cross-sectional view schematically showing a state where the cuff is wrapped around a living body.
Figure 4:
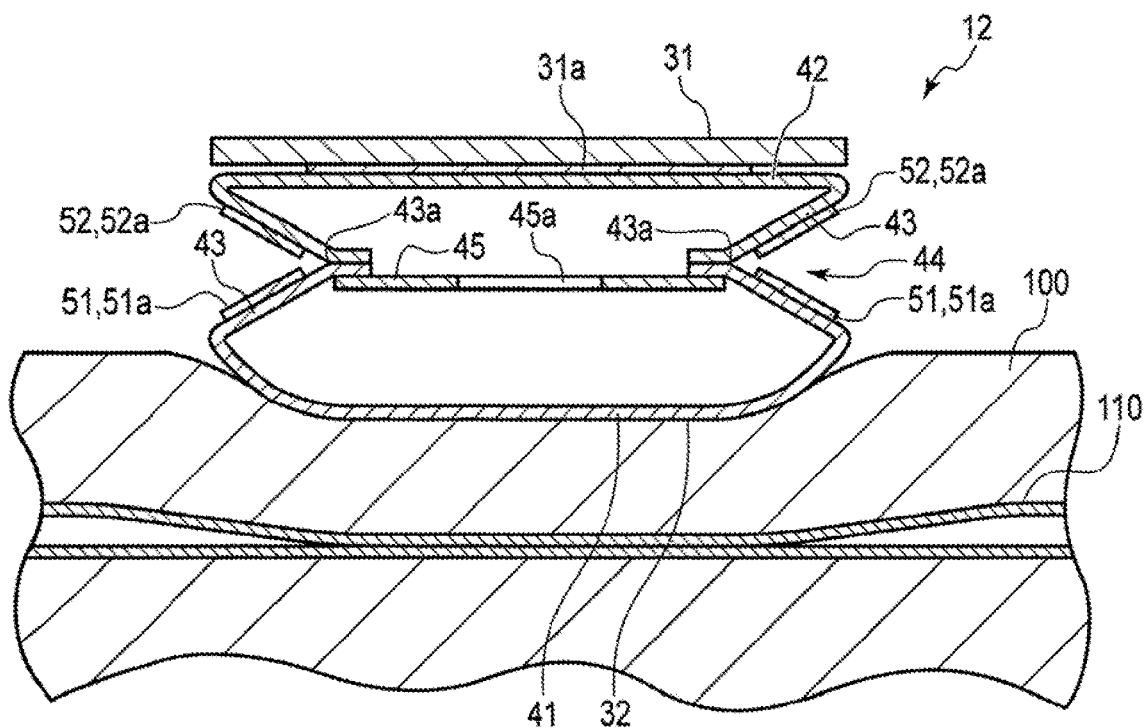
FIG. 4 is a cross-sectional view schematically showing a state where the cuff is inflated with the cuff wrapped around the living body.
Figure 8:
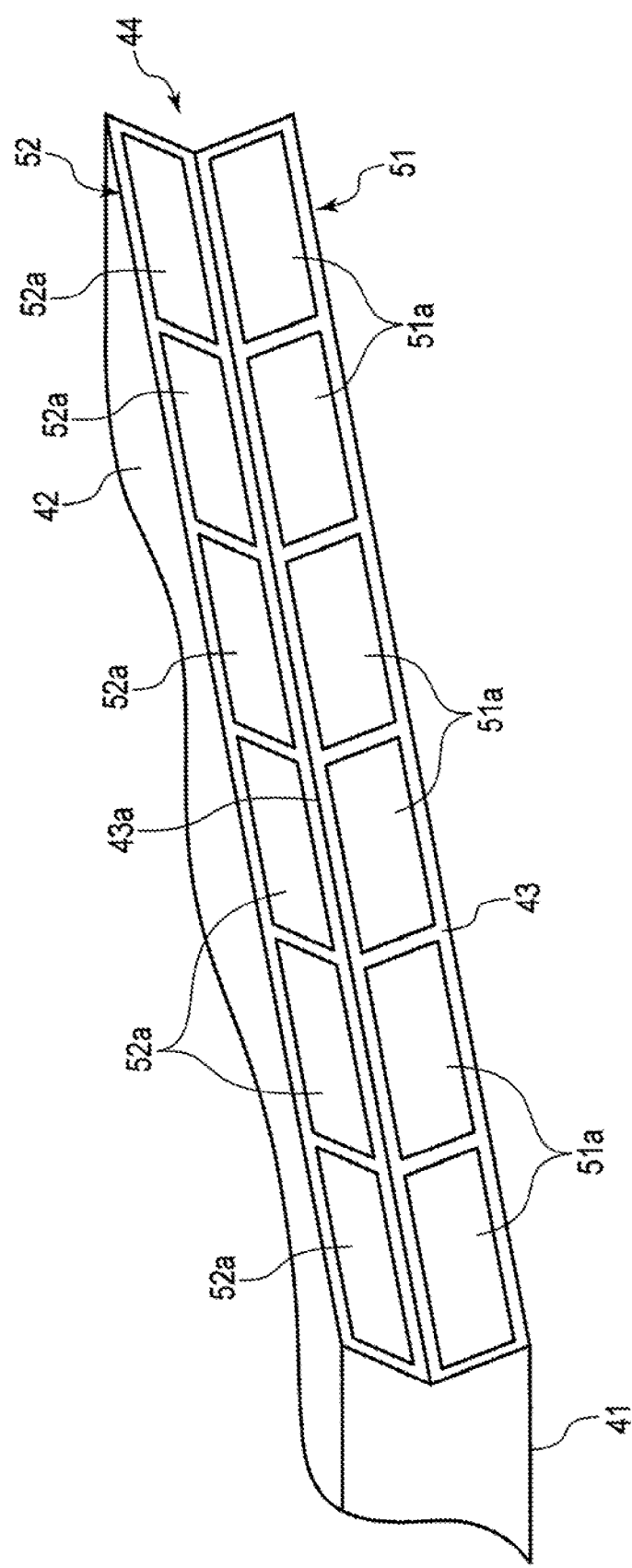
FIG. 8 is a cross-sectional view showing configurations of a side wall portion and reinforcing member of the bag-shaped structure.

FIG. 1 is a perspective view showing a configuration of the blood pressure monitor 1 according to the embodiment of the present invention, FIG. 2 is a cross-sectional view showing a configuration of the cuff 12 used in the blood pressure monitor 1, FIG. 3 is a cross-sectional view schematically showing a state where the cuff 12 is wrapped around a wrist 100 of a living body, and FIG. 4 is a cross-sectional view schematically showing a state where the bag-shaped structure 32 of the cuff 12 is inflated with the cuff 12 wrapped around the wrist 100, and is compressing an artery 110. FIGS. 5 and 6 are partially-cutaway perspective views showing a configuration of the bag-shaped structure 32 used in the cuff 12. FIG. 7 is a side view schematically showing a configuration of the bag-shaped structure 32 in the state of being wrapped around the wrist 100 of the living body, in a direction orthogonal to the wrapping direction. FIG. 8 is a perspective view showing configurations of a side wall portion 43 and reinforcing member 44 of the bag-shaped structure 32.

The blood pressure monitor 1 is an electronic blood pressure monitor to be worn on a living body, for example, the wrist 100. As shown in FIG. 1, the blood pressure monitor 1 includes an apparatus main body 11 and a cuff 12.

The apparatus main body 11 includes a case 21, a display 22, an operation unit 23, a pump 24, a on-off valve 25, a pressure sensor 26, a power supply unit 27, and a controller 28. The apparatus main body 11 also includes an air flow path that fluidly connects the pump 24, the on-off valve 25, the pressure sensor 26, and the cuff 12. For example, the air flow path is formed by arranging a tube or the like made of a resin material or the like in the case 21.

The display 22 is arranged on the upper surface of the case 21. The case 21 houses the pump 24, the on-off valve 25, the pressure sensor 26, the power supply unit 27, and the controller 28. The case 21 is integrally connected to the cuff 12.

The display 22 is electrically connected to the controller 28. The display 22 is, for example, a liquid crystal display or an organic electroluminescence display. The display 22 displays various information including measurements such as blood pressure values, e.g., a systolic blood pressure and a diastolic blood pressure, and a heart rate.

The operation unit 23 is configured to receive a command from the user. For example, the operation unit 23 is a button provided on the case 21, or a touch panel provided on the display. The operation unit 23 converts the command into an electrical signal in response to a user's operation. The operation unit 23 is electrically connected to the controller 28 and outputs the electrical signal to the controller 28.

The pump 24 is, for example, a rolling pump. The pump 24 compresses air, and supplies compressed air to the cuff 12 via the flow path. The pump 24 is electrically connected to the controller 28.

The on-off valve 25 is an electromagnetic valve electrically connected to the controller 28. The on-off valve 25 is opened and closed in accordance with the command from the controller 28. When being opened, the on-off valve 25 makes the flow path continuous with the atmosphere and reduces the pressure in the flow path.

The pressure sensor 26 detects the pressure in the flow path. The pressure sensor 26 is electrically connected to the controller 28, converts the detected pressure into an electrical signal, and outputs it to the controller 28. Here, since the flow path is continuous with the bag-shaped structure 32 (to be described later) of the cuff 12, the pressure in the flow path is equal to the pressure in the internal space of the bag-shaped structure 32.

The power supply unit 27 is, for example, a secondary battery such as a lithium ion battery. The power supply unit 27 is electrically connected to the controller 28. The power supply unit 27 supplies power to the controller 28.

The controller 28 supplies power to the display 22, the operation unit 23, the pump 24, the on-off valve 25, and the pressure sensor 26. The controller 28 also controls the operations of the display 22, the pump 24, and the on-off valve 25 based on the electrical signals output from the operation unit 23 and the pressure sensor 26.

For example, when a command to measure a blood pressure is input from the operation unit 23, the controller 28 drives the pump 24 and sends compressed air to the cuff 12. Furthermore, the controller 28 controls whether to drive or stop the pump 24 and whether to open or close the on-off valve 25 based on the electrical signal output by the pressure sensor 26. Moreover, the controller 28 obtains measurements such as a blood pressure value, e.g., a systolic blood pressure or a diastolic blood pressure, and a heart rate from the electrical signal output by the pressure sensor 26, and outputs an image signal corresponding to the measurements to the display 22.

As shown in FIGS. 1 and 2, the cuff 12 includes a base 31 and a bag-shaped structure 32. The cuff 12 is fixed to the wrist by being wrapped around the wrist.

The base 31 is curved along the shape of the wrist 100 of the living body. For example, the base 31 has one end formed integrally with the case 21, and the other end fixable to the case 21 with a fastener or the like. The base 31 supports the bag-shaped structure 32 on its inner surface. For example, the base 31 includes, on its inner surface, a joint layer 31a such as an adhesive or a double-sided tape for joining the bag-shaped structure 32 thereto. The base 31 is made of a hard resin material.

As shown in FIGS. 2 to 8, the bag-shaped structure 32 includes: a rectangular inner wall portion 41 elongated in one direction; a rectangular outer wall portion 42 elongated in one direction; a pair of side wall portions 43 joining the inner wall portion 41 and the outer wall portion 42 and bent toward the inside of the bag-shaped structure 32; and a reinforcing member 44 provided on each of the pair of side wall portions 43. The bag-shaped structure 32 also includes: a junction 45 which connects the pair of side wall portions 43 in a direction orthogonal to the longitudinal direction of the bag-shaped structure 32; and a connection tube 46 fluidly connecting an internal space formed by the inner wall portion 41, the outer wall portion 42, and the pair of side wall portions 43 to the flow path of the apparatus main body 11.

In the bag-shaped structure 32, an air chamber fluidly connected to the flow path of the apparatus main body 11 is formed by the inner wall portion 41, the outer wall portion 42, and the pair of side wall portions 43. The bag-shaped structure 32 is arranged on the base 31 in such a manner that the longitudinal direction thereof is curved along the inner surface of the base 31. The width of the bag-shaped structure 32 is, for example, 40 mm or less. Such a bag-shaped structure 32 is sometimes called a Σ structure or bellows structure because the side wall portions 43 are bent toward the inside of the bag-shaped structure 32.

The bag-shaped structure 32 is configured by, from the state where the both ends are open as shown in FIG. 6, joining the inner wall portion 41 and the outer wall portion 42 at both longitudinal ends with the connection tube 46 interposed therebetween at one end as shown in FIG. 5. The bag-shaped structure 32 is formed by, for example, integrally joining a plurality of sheet members each having a predetermined shape and made of a thermoplastic elastomer.

As the thermoplastic elastomer constituting each sheet member, for example, thermoplastic polyurethane resin (hereinafter referred to as TPU), polyvinyl chloride resin, ethylene-vinyl acetate resin, thermoplastic polystyrene resin, thermoplastic polyolefin resin, thermoplastic polyester resin, or thermoplastic polyamide resin can be used. As the thermoplastic elastomer, TPU is preferably used. The sheet member may have a single-layer structure, or may have a multi-layer structure.

The sheet member is not limited to the thermoplastic elastomer, and may be a thermoset elastomer such as silicone, or a combination of a thermoplastic elastomer (such as TPU) and a thermoset elastomer (such as silicone).

When a thermoplastic elastomer is used for the sheet member, a molding method such as T-die extrusion molding or injection molding is used, and when a thermoset elastomer is used, a molding method such as mold casting is used. After being molded by each molding method, the sheet member is sized to a predetermined shape, and sized pieces are joined by bonding, welding, or the like to form the bag-shaped structure 32. As the joining method, a molding method such as high frequency welder or laser welding is used when a thermoplastic elastomer is used, and a molecular adhesive is used when a thermosetting elastomer is used.

The sheet member has a Shore A hardness in the range from 15 to 95. This is because, when the Shore A hardness is less than 15, there is a high possibility that the durability is impaired when the bag-shaped structure 32 is repeatedly inflated and deflated, and when the Shore A hardness is greater than 95, the inflation pressure of the bag-shaped structure 32 increases and the load on the living body increases. The Shore A hardness refers to a durometer hardness obtained by a Type A durometer hardness test as specified in JIS K6253-3:2012 ("Rubber, vulcanized or thermoplastic—Determination of hardness—Part 3: Durometer hardness").

The inner wall portion 41 is arranged on the living body side. The outer wall portion 42 is arranged to face the inner wall portion 41.

The outer wall portion 42 is arranged on the base 31 side.

In the side wall portion 43, a bent portion 43a bent toward the internal space of the bad-shaped structure 32 is provided at substantially the center as viewed in a direction in which the inner wall portion 41 faces the outer wall portion 42. The bent portion 43a may be provided when sheet members are joined, or provided by shaping sheet members through molding.

The reinforcing member 44 is made of a material having a higher hardness than the side wall portion 43. The material used for the reinforcing member 44 is, for example, acrylonitrile butadiene styrene, polyethylene terephthalate, polycarbonate, polypropylene, or polyimide.

Before the bag-shaped structure 32 is fixed to the base 31, the reinforcing member 44 is provided along the direction in which the bag-shaped structure 32 extends. The reinforcing member 44 has shape followability in a direction of wrapping around the wrist 100 so that the reinforcing member 44 extends along the direction of wrapping around the wrist 100 when the bag-shaped structure 32 is provided on the base 31 and bent around the shape of the wrist 100.

The shape followability is a property that enables the bag-shaped structure 32 provided with the reinforcing member 44 to change in shape in accordance with the shape of the contact portion of the wrist 100 when wrapped around the wrist 100. Namely, the reinforcing member 44 having shape followability means a reinforcing member 44 capable of, when provided in the bag-shaped structure 32, providing the bag-shaped structure 32 with a property to roughly follow the shape of the contact portion of the wrist 100. Therefore, the reinforcing member 44 having shape followability does not need to have a property that enables the reinforcing member 44 itself to change in shape so that the bag-shaped structure 33 follows the shape of the contact portion of the wrist 100 to such an extent that the outer surface of the inner wall portion 41 of the bag-shaped structure 32, which comes into contact with the wrist 100, comes into close contact with the wrist 100.

The shape followability of the reinforcing member 44 can be attained by dividing the reinforcing member 44 in the wrapping direction or providing the reinforcing member 44 itself with high flexibility. In the present embodiment, descriptions will be provided by using the configuration in which the reinforcing member 44 is divided in the wrapping direction, as shown in FIGS. 5 to 8.

Furthermore, the reinforcing member 44 has a hardness and shape that can prevent a crease, i.e., an unintended crease, in the side wall portion 43 when the bag-shaped structure 32 is wrapped around the wrist 100.

The reinforcing member 44 is provided on each of the pair of side wall portions 43. The thickness of the reinforcing member 44 is in the range from 0.01 mm to 1.00 mm. This is because the reinforcing member 44 with a thickness of less than 0.01 mm cannot sufficiently reinforce the side wall portion 43, and the reinforcing member 44 with a thickness of more than 1.00 mm causes the side wall portion 43 to have a bulky thickness and lowers usability, such as appearance and wearability, of the cuff 12 when the bag-shaped structure 32 is folded.

As shown in FIGS. 7 and 8, the reinforcing member 44 includes a first reinforcing member 51 provided on the inner wall portion 41 side with respect to the bent portion 43a of the side wall portion 43, and a second reinforcing member 52 provided on the outer wall portion 42 side with respect to the bent portion 43a. To prevent the reinforcing member 44 from inhibiting the joint in the bag-shaped structure 32, the reinforcing member 44 is provided away from the joint portion.

The first reinforcing member 51 includes a plurality of small pieces 51a arranged in the longitudinal direction of the side wall portion 43. The small piece 51a is a rectangular thin plate made of a resin material. The small piece 51a is fixed to the outer surface of the side wall portion 43 by an adhesive or the like.

The small pieces 51a are set so that the gap between adjacent small pieces 51a is larger than the thickness of the small piece 51a and equal to or smaller than 2 mm. This is because, if the width of the gap is smaller than the thickness of the small piece 51a, the small pieces 51a interfere with each other, and if the width exceeds the upper limit value, the side wall portion 43 between small pieces 51a may expand by the inflation pressure in the air chamber of the bag-shaped structure 32.

For example, the length of the small piece 51a in the longitudinal direction of the side wall portion 43 is 10 mm. In addition, for example, the length of the small piece 51a in the direction orthogonal to the longitudinal direction of the side wall portion 43 is a length that allows the small piece 51a to be arranged on the side wall portion 43 with a 0.3 mm to 0.5 mm distance from each of the end on the inner wall portion 41 side of the side wall portion 43 and the end on the bent portion 43a side. Preferably, the edge of the small piece 51a is chamfered to be round.

The second reinforcing member 52 includes a plurality of small pieces 52a arranged in the longitudinal direction of the side wall portion 43. The small piece 52a is a rectangular thin plate made of a resin material. The small piece 52a is fixed to the outer surface of the side wall portion 43 by an adhesive or the like.

The small pieces 52a are set so that the gap between adjacent small pieces 52a is larger than the thickness of the small piece 52a and equal to or smaller than 2 mm. This is because, if the width of the gap is smaller than the thickness of the small piece 52a, the small pieces 52a interfere with each other, and if the width exceeds the upper limit value, the side wall portion 43 between small pieces 52a may expand by the inflation pressure in the air chamber of the bag-shaped structure 32.

For example, the length of the small piece 52a in the longitudinal direction of the side wall portion 43 is 10 mm. In addition, for example, the length of the small piece 52a in the direction orthogonal to the longitudinal direction of the side wall portion 43 is a length that allows the small piece 52a to be arranged on the side wall portion 43 with a 0.3 mm to 0.5 mm distance from each of the end on the outer wall portion 42 side of the side wall portion 43 and the end on the bent portion 43a side. Preferably, the edge of the small piece 52a is chamfered to be round. Namely, the second reinforcing member 52 has the same configuration as the first reinforcing member 51 in the present embodiment.

The junction 45 connects the bent portions 43a of the pair of side wall portions 43. The junction 45 includes a plurality of openings 45a for preventing fluid division in the air chamber, i.e., for making the inner wall portion 41 side and the outer wall portion 42 side of the air chamber divided by the junction 45 continuous with each other.

The connection tube 46 is made of, for example, a resin material and is flexible. The connection tube 46 is fixed to one longitudinal end of the bag-shaped structure 32. The connection tube 46 has one end connected to the internal space of the bag-shaped structure 32 to be connected to the flow path of the apparatus main body 11. The connection tube 46 constitutes an air flow path from the flow path of the apparatus main body 11 to the air chamber of the bag-shaped structure 32.

In such a bag-shaped structure 32, the reinforcing member 44 is fixed to the side wall portion 43 by arranging a plurality of small pieces 51a and small pieces 52a applied with an adhesive in a predetermined arrangement, and then pressing the side wall portion 43 to the reinforcing member 44.

Next, measurement of a blood pressure value using the blood pressure monitor 1 will be described with reference to FIGS. 1, 3, and 4.

When measuring a blood pressure value, the user wears the cuff 12 on the living body, which is the wrist 100 in the present embodiment. As a result, the bag-shaped structure 32 of the cuff 12 comes into contact with the wrist 100, as shown in FIG. 3. Next, the user operates the operation unit 23 shown in FIG. 1 and inputs a command corresponding to the start of measurement of a blood pressure value.

The operation unit 23 to which the command input operation has been performed outputs an electrical signal corresponding to the start of measurement to the controller 28. Upon receipt of the electrical signal, the controller 28 closes the on-off valve 25, drives the pump 24, and supplies compressed air to the bag-shaped structure 32 via the flow path. As a result, the bag-shaped structure 32 starts to inflate.

The pressure sensor 26 detects the pressure in the internal space of the bag-shaped structure 32, and outputs an electrical signal corresponding to the pressure to the controller 28. Based on the received electrical signal, the controller 28 determines whether or not the pressure in the internal space of the bag-shaped structure 32 has reached a predetermined pressure for blood pressure measurement. When the pressure in the internal space of the bag-shaped structure 32 reaches the predetermined pressure, the controller 28 stops driving the pump 24. At this time, as shown in FIG. 4, the bag-shaped structure 32 has been sufficiently inflated, and the inflated bag-shaped structure 32 compresses the wrist and blocks the artery 110 in the wrist 100.

Thereafter, the controller 28 controls the on-off valve 25 to repeatedly open and close the on-off valve 25 or adjust the opening degree of the on-off valve 25 to reduce the pressure in the internal space of the bag-shaped structure 32. Based on the electrical signal output by the pressure sensor 26 in this process of reducing the pressure, the controller 28 obtains measurements such as blood pressure values, e.g., a systolic blood pressure and a diastolic blood pressure, a heart rate, and the like. The controller 28 outputs an image signal corresponding to the obtained measurements to the display 22.

Upon receipt of the image signal, the display 22 displays the measurements on the screen. The user looks at the display 22 to ascertain the measurements. After the measurement is completed, the user unfastens the fastener and removes the blood pressure monitor 1 from the wrist.

In the cuff 12 used in the blood pressure monitor 1 according to one embodiment configured as described above, the reinforcing member 44 including a plurality of small pieces 51a and 52a is provided on the side wall portion 43 of the bag-shaped structure 32. With this configuration, the bag-shaped structure 32 can suppress expansion of the side wall portion 43 by means of the small pieces 51a and 52a when inflated by the air supplied to the inside thereof.

Since the reinforcing member 44 prevents expansion of the side wall portion 43, the bag-shaped structure 32 can prevent a loss of the inflation pressure in the air chamber caused by the expansion of the side wall portion 43. As a result, the inner wall portion 41 is more inflated, and the vascular compression property can be improved. Furthermore, the reinforcing member 44 can prevent a crease in the side wall portion 43, etc. when the bag-shaped structure 32 is wrapped around the wrist 100, and thus can realize a stable vascular compression property.

By providing the reinforcing member 44 on the side wall portion 43 in such a manner that a plurality of small pieces 51a and a plurality of small pieces 52a are arranged at predetermined intervals, the side wall portion 43 can bend between small pieces 51a and between small pieces 52a. Therefore, the side wall portion 43 of the bag-shaped structure 32 has shape followability to follow the shape of the wrist 100. As a result, the bag-shaped structure 32 can follow the shape of the wrist 100 when the cuff 12 is wrapped around the wrist 100, and can achieve closer contact of the bag-shaped structure 32 with the living body as the inner wall portion 41 is brought into close contact with the surface of the wrist 100 even though the reinforcing member 44 is provided.

Accordingly, the cuff 12 can realize a high wave measurement property even when the bag-shaped structure 32 with a reduced cuff width is used, and the blood pressure monitor 1 can attain high blood pressure measurement accuracy.

In addition, since the first reinforcing member 51 and the second reinforcing member 52 of the reinforcing member 44 are provided away from the bent portion 43a of the side wall portion 43, the reinforcing member 44 does not inhibit inflation or deflation of the bag-shaped structure 32 when the bag-shaped structure 32 is inflated or deflated.

As described above, the blood pressure monitor 1 according to the embodiment includes the reinforcing member 44 having shape followability to the wrist 100 is provided on the side wall portion 43 of the bag-shaped structure 32, and thus can suppress expansion of the side wall portion 43 and improve the vascular compression property while keeping shape followability of the bag-shaped structure 32 to the wrist 100.

[Modifications]

Next, first to eleventh modifications of the bag-shaped structure 32 will be described with reference to FIGS. 9 to 19. Each modification is of a bag-shaped structure used in the cuff 12 for the blood pressure monitor 1 according to the above-described embodiment, and descriptions of structures other than the bag-shaped structure will be omitted. Of the structures of each modification, the same structures as those of the blood pressure monitor 1 according to the above-described embodiment are assigned with the same reference numerals as those of the blood pressure monitor 1 according to the above-described embodiment, and detailed descriptions will be omitted.

Figure 9:
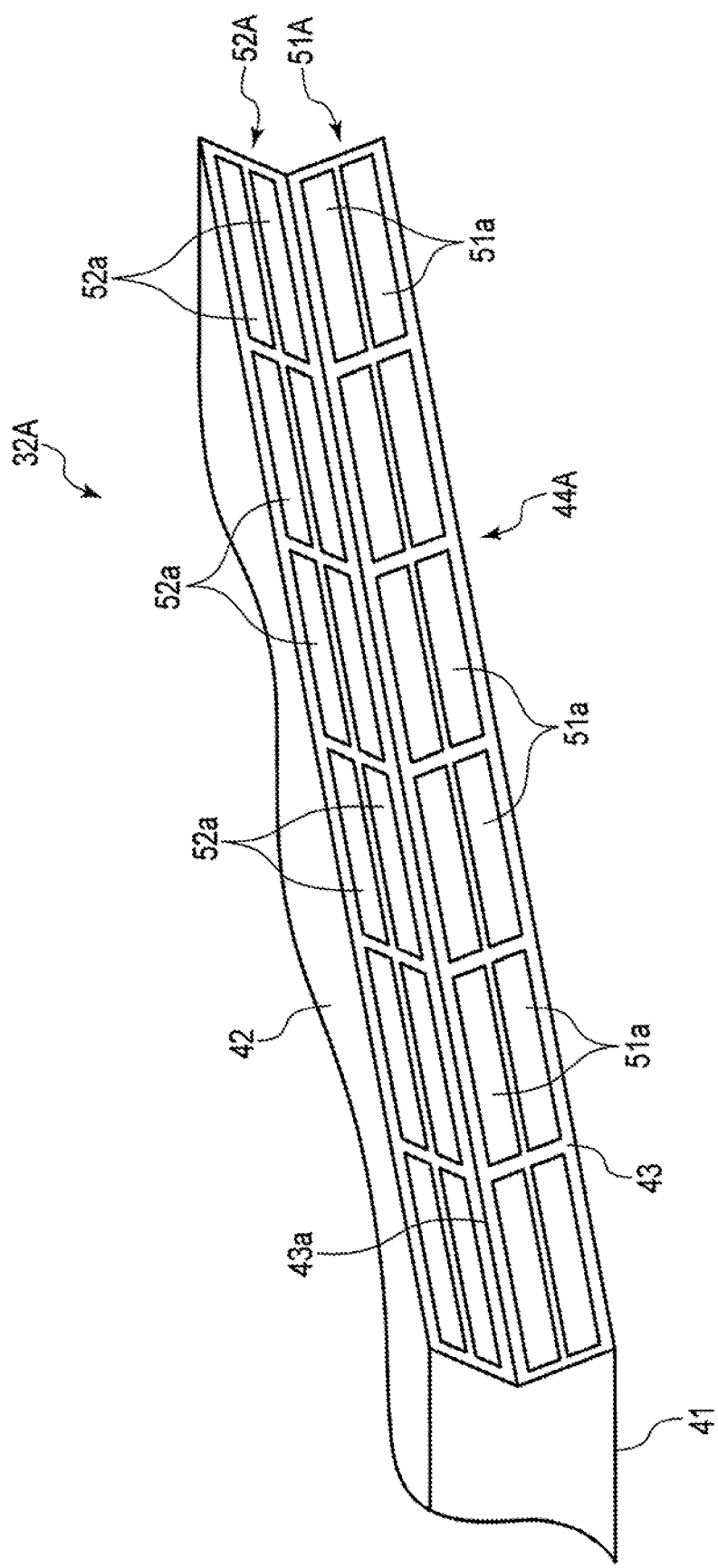
FIG. 9 is a perspective view schematically showing a configuration of a bag-shaped structure according to a first modification of the present invention.
Figure 10:
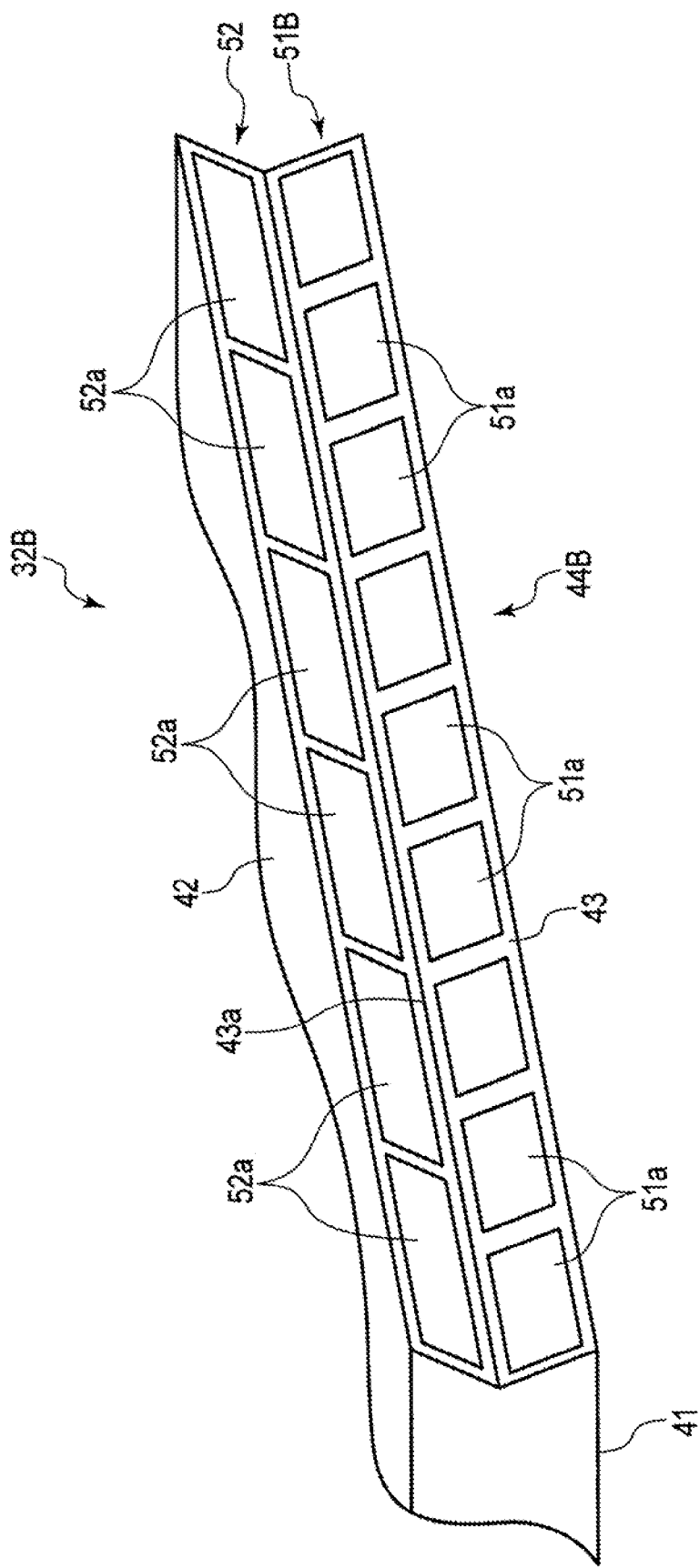
FIG. 10 is a perspective view schematically showing a configuration of a bag-shaped structure according to a second modification of the present invention.
Figure 11:
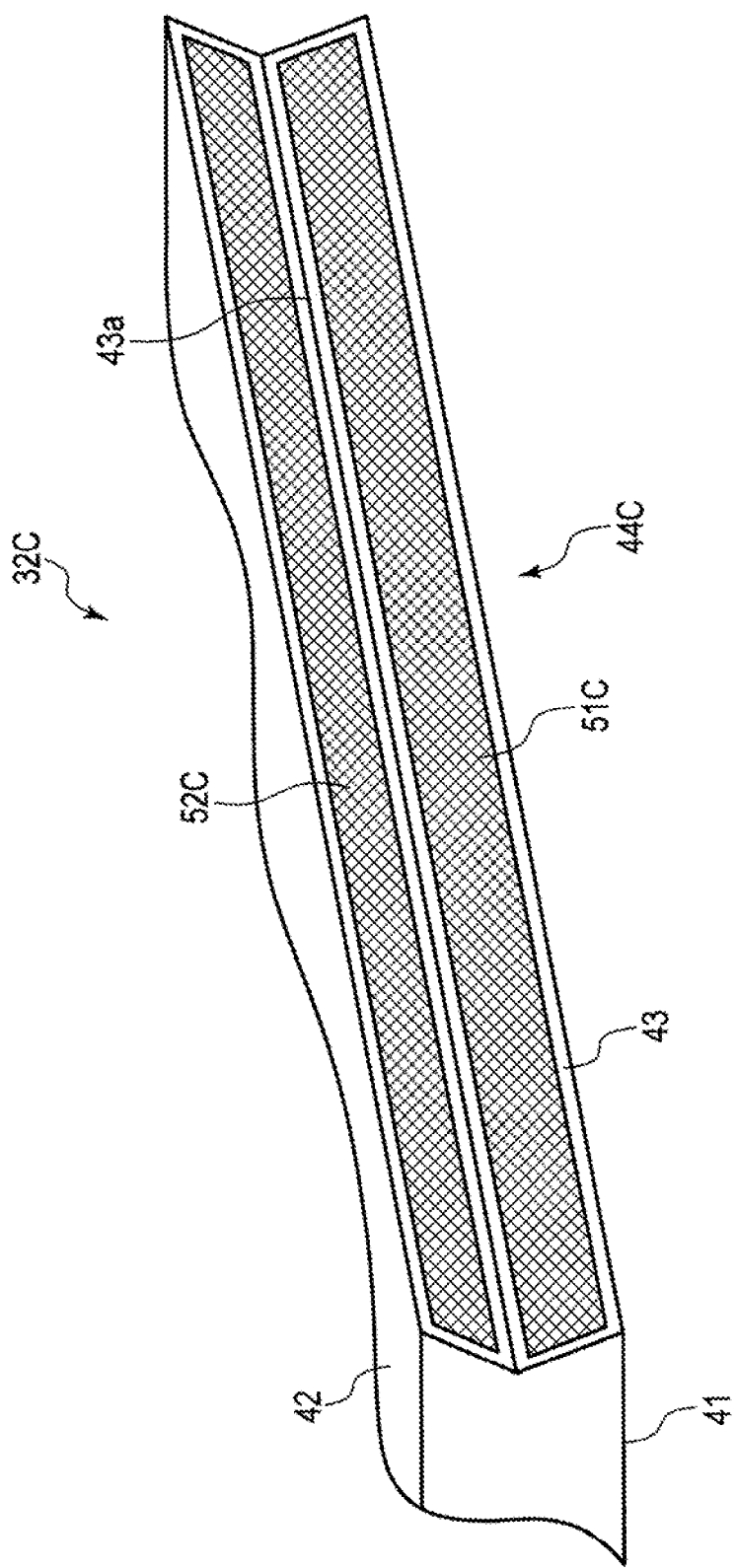
FIG. 11 is a perspective view schematically showing a configuration of a bag-shaped structure according to a third modification of the present invention.
Figure 12:
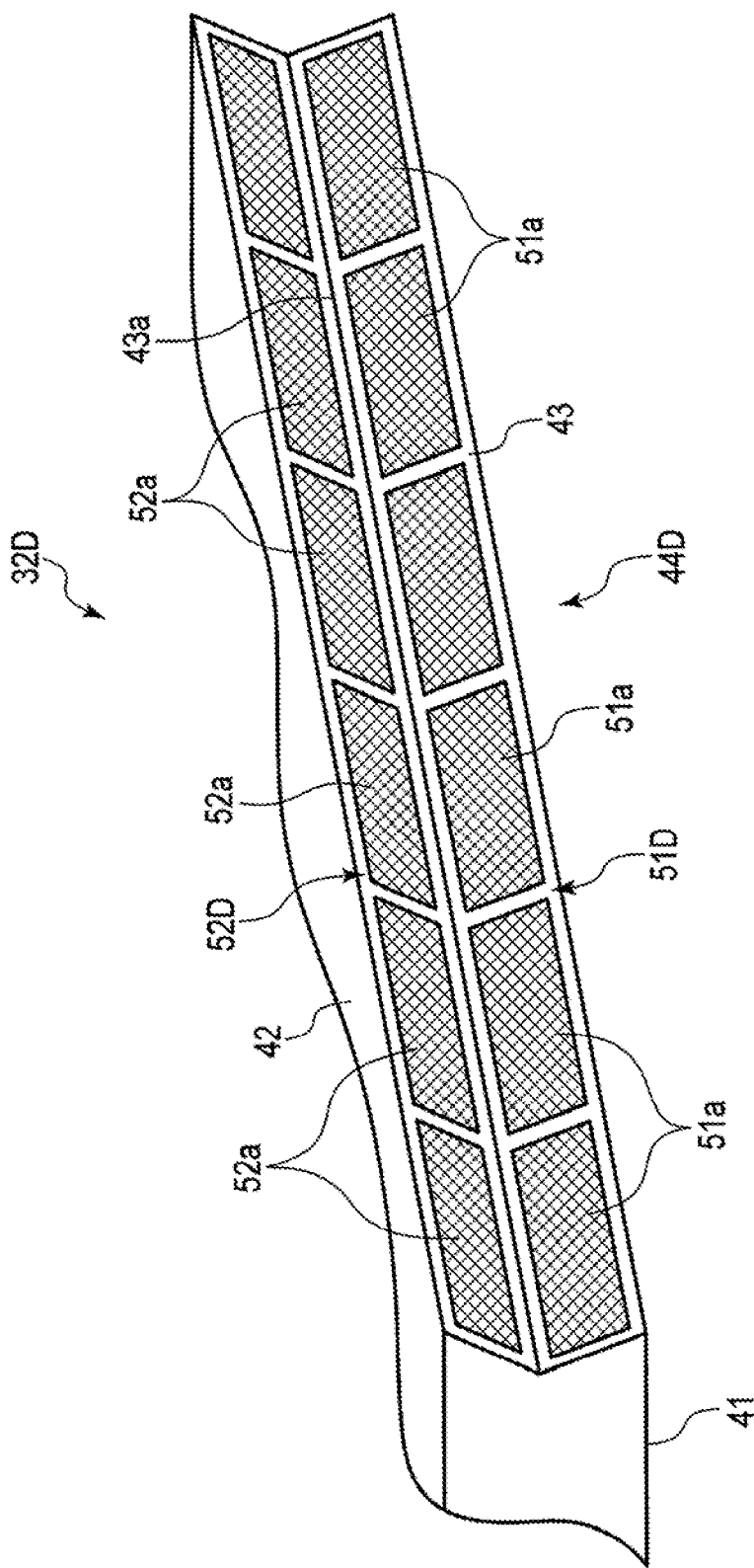
FIG. 12 is a perspective view schematically showing a configuration of a bag-shaped structure according to a fourth modification of the present invention.
Figure 13:
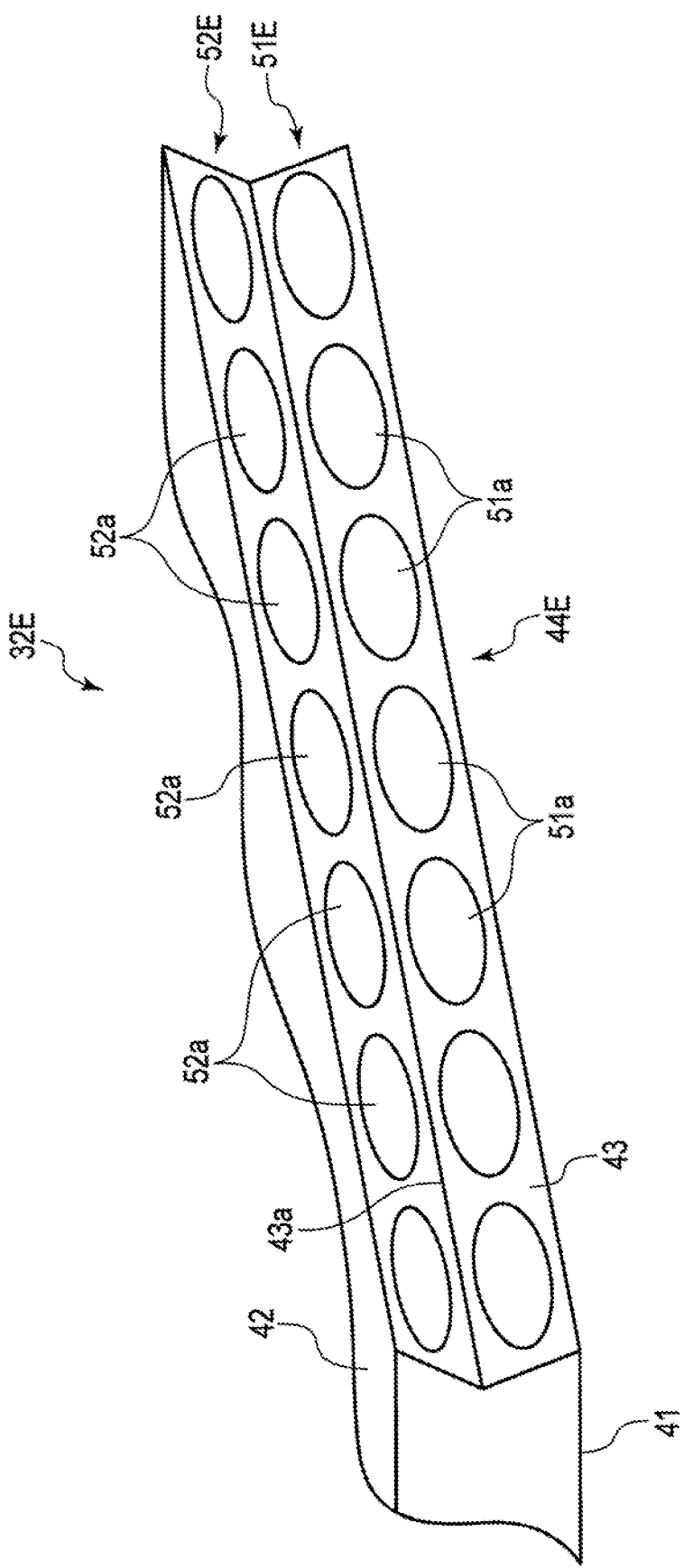
FIG. 13 is a perspective view schematically showing a configuration of another example of a bag-shaped structure according to a fifth modification of the present invention.
Figure 14:
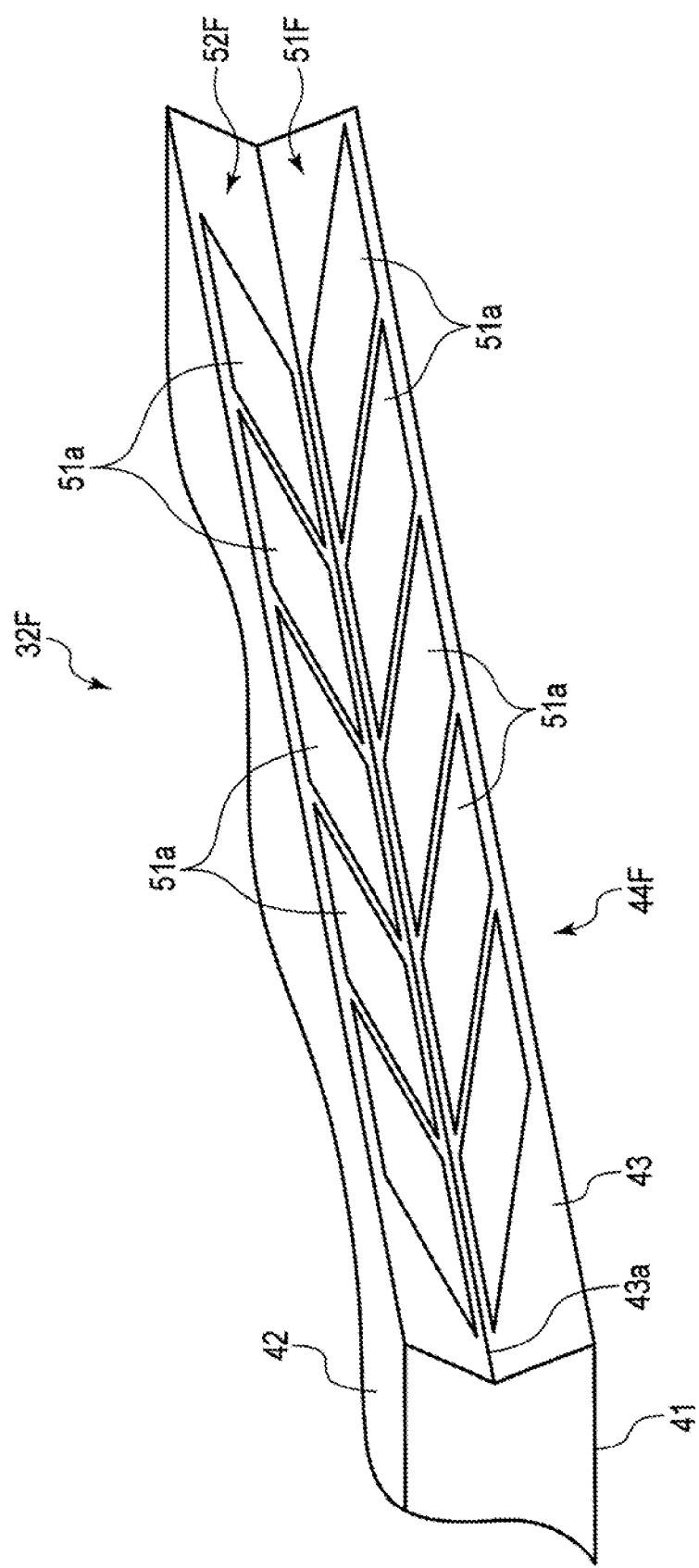
FIG. 14 is a perspective view schematically showing a configuration of a bag-shaped structure according to a sixth modification of the present invention.
Figure 15:
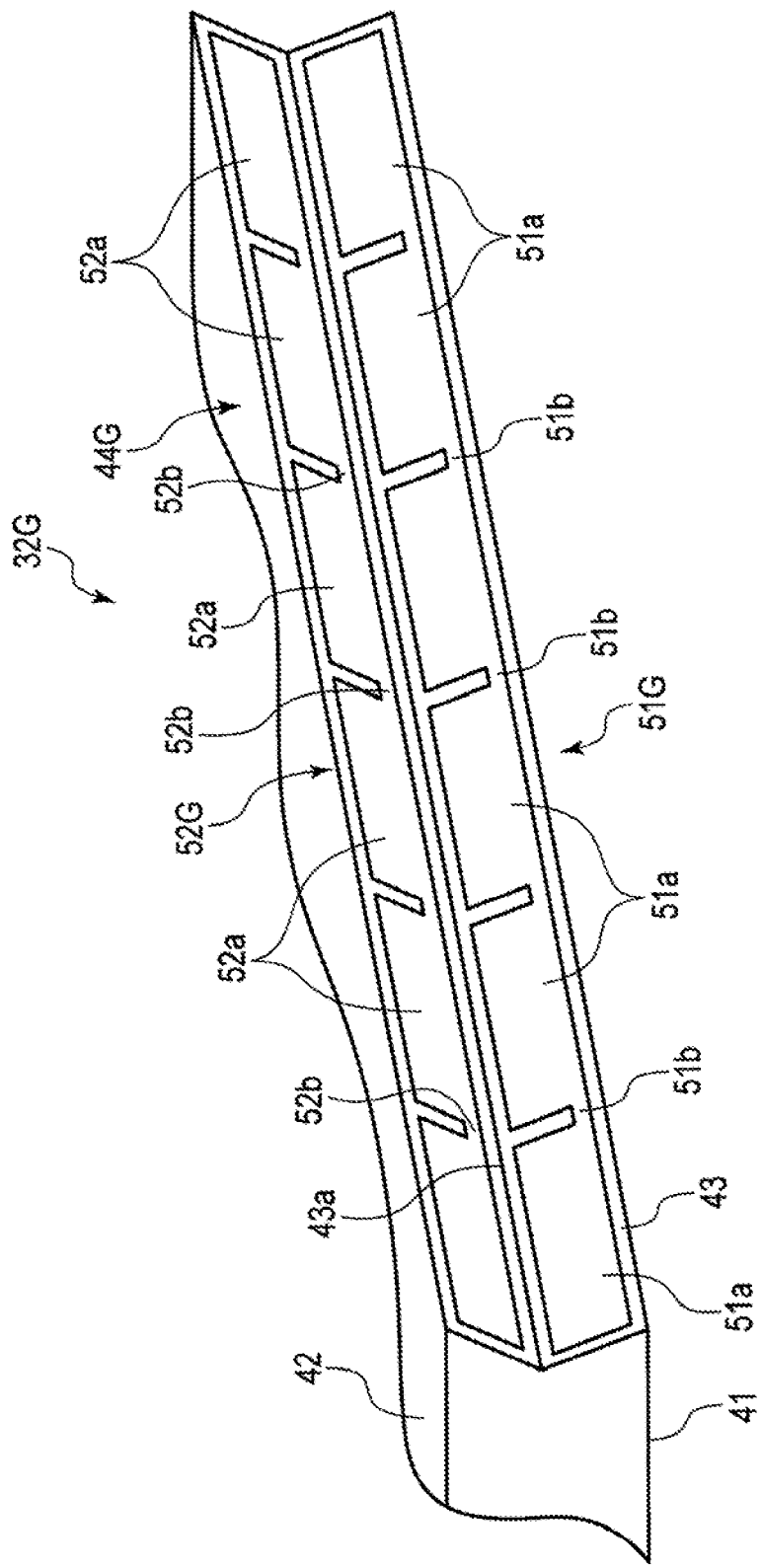
FIG. 15 is a perspective view schematically showing a configuration of a bag-shaped structure according to a seventh modification of the present invention.
Figure 16:
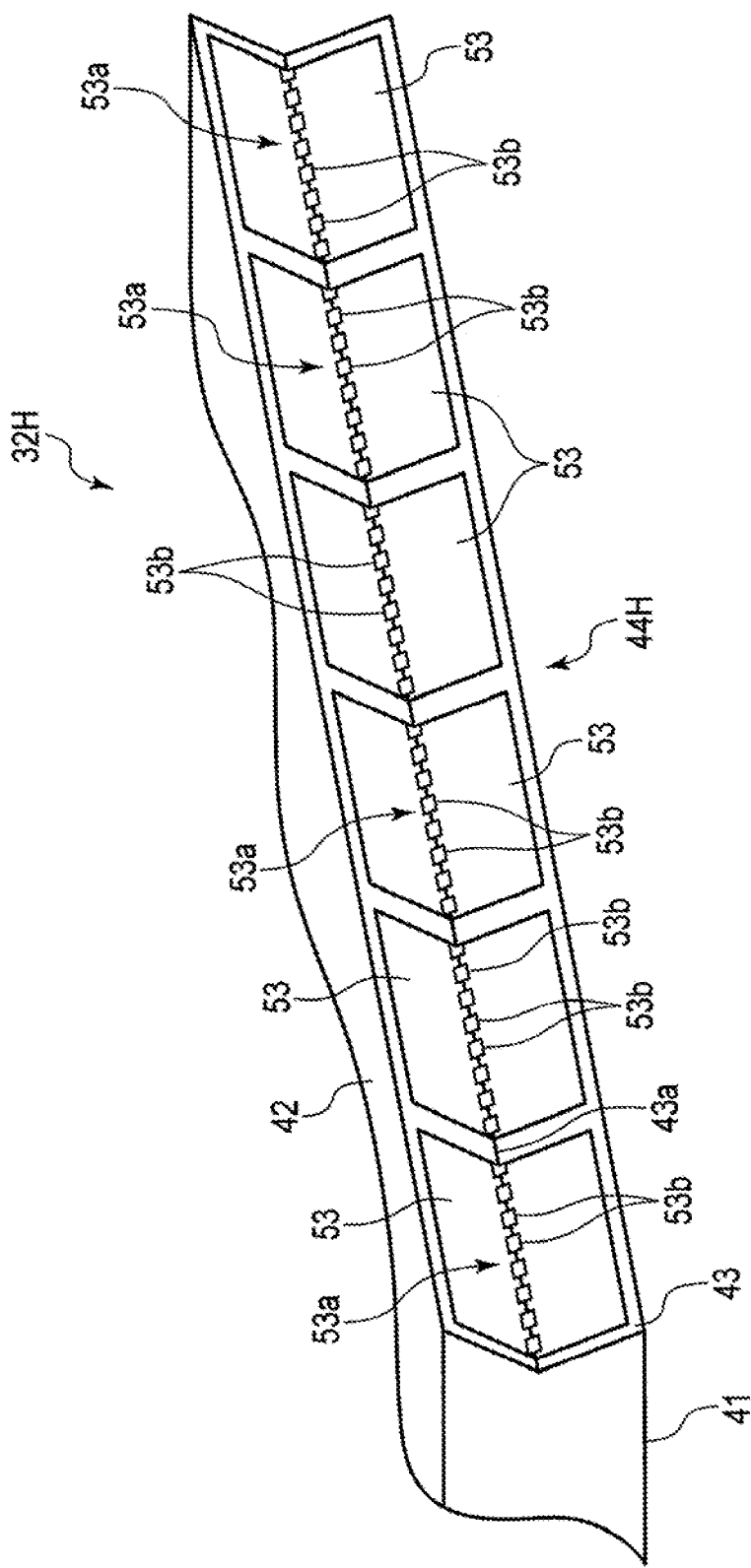
FIG. 16 is a perspective view schematically showing a configuration of a bag-shaped structure according to an eighth modification of the present invention.
Figure 17:
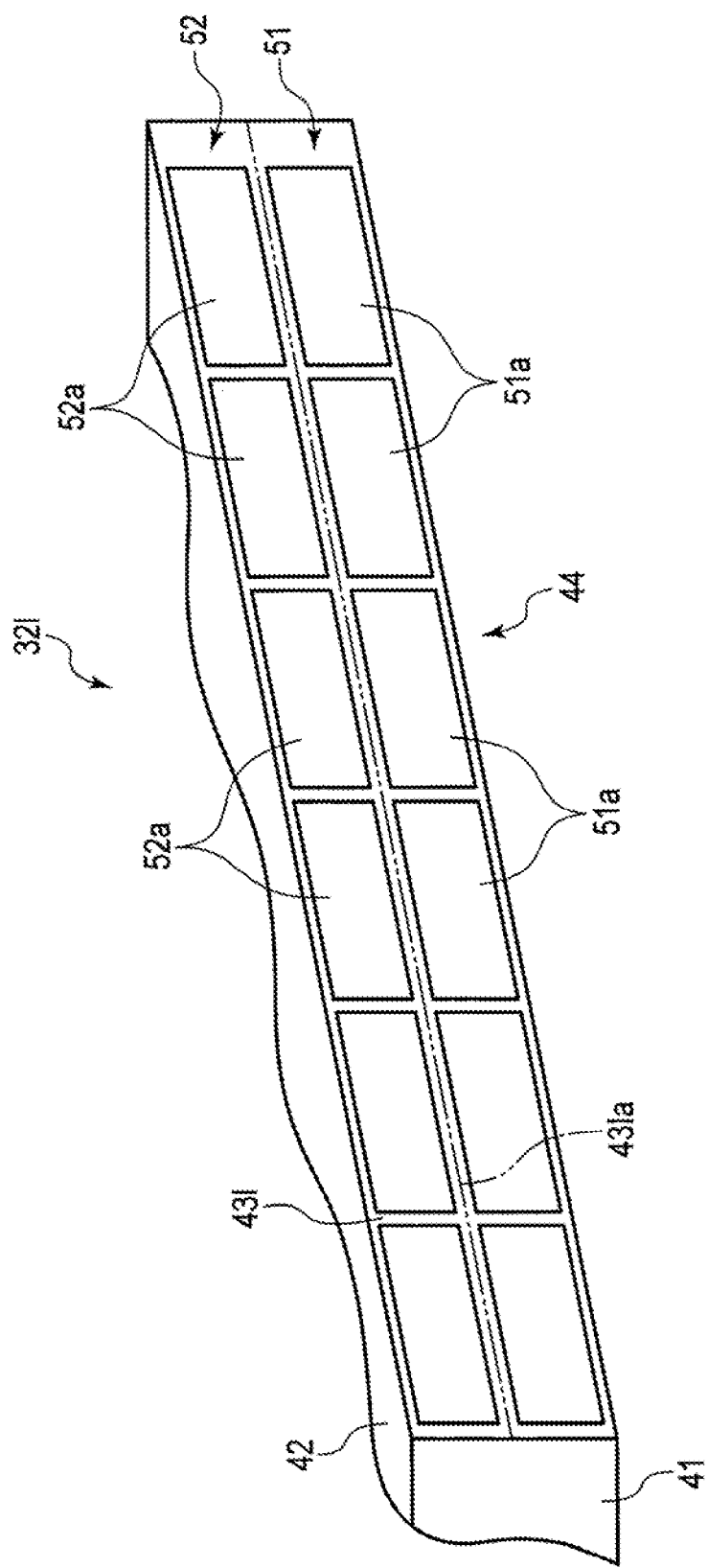
FIG. 17 is a perspective view schematically showing a configuration of a bag-shaped structure according to a ninth modification of the present invention.

FIG. 9 is a perspective view schematically showing a configuration of a bag-shaped structure 32A according to the first modification, FIG. 10 is a perspective view schematically showing a configuration of a bag-shaped structure 32B according to the second modification, FIG. 11 is a perspective view schematically showing a configuration of a bag-shaped structure 32C according to the third modification, FIG. 12 is a perspective view schematically showing a configuration of a bag-shaped structure 32D according to the fourth modification, FIG. 13 is a perspective view schematically showing a configuration of a bag-shaped structure 32E according to the fifth modification, and FIG. 14 is a perspective view schematically showing a configuration of a bag-shaped structure 32F according to the sixth modification, FIG. 15 is a perspective view schematically showing a configuration of a bag-shaped structure 32G according to the seventh modification, FIG. 16 is a perspective view schematically showing a configuration of a bag-shaped structure 32H according to the eighth modification, FIG. 17 is a perspective view schematically showing a configuration of a bag-shaped structure 32I according to the ninth modification, FIG. 18 is a cross-sectional view schematically showing a configuration of a bag-shaped structure 32J according to the tenth modification, and FIG. 19 is a cross-sectional view schematically showing a configuration of a bag-shaped structure 32K according to the eleventh modification.

[First Modification]

As shown in FIG. 9, the bag-shaped structure 32A according to the first modification includes an inner wall portion 41, an outer wall portion 42, a pair of side wall portions 43, and a reinforcing member 44A provided on each of the pair of side wall portions 43. The bag-shaped structure 32A also includes a junction 45 and a connection tube 46, although they are omitted in FIG. 9.

The reinforcing member 44A is made of the same material as that of reinforcing member 44. The reinforcing member 44A has shape followability in the direction of wrapping around the wrist 100 as it is divided in the wrapping direction. The thickness of the reinforcing member 44A is in the range from 0.01 mm to 1.00 mm.

As shown in FIG. 9, the reinforcing member 44A includes a first reinforcing member 51A provided on the inner wall portion 41 side with respect to the bent portion 43a of the side wall portion 43, and a second reinforcing member 52A provided on the outer wall portion 42 side with respect to the bent portion 43a.

The first reinforcing member 51A includes two lines of a plurality of small pieces 51a arranged in the longitudinal direction of the side wall portion 43. The two lines are aligned in the direction in which the inner wall portion 41 faces the outer wall portion 42. The small piece 51a is a rectangular thin plate. The small piece 51a is fixed to the outer surface of the side wall portion 43 by an adhesive or the like.

The small pieces 51a are set so that the gap between small pieces 51a adjacent to each other in the longitudinal direction of the side wall portion 43 is larger than the thickness of the small piece 51a and equal to or smaller than 2 mm. The length of the small piece 51a in the longitudinal direction of the side wall portion 43 is 10 mm. In addition, for example, the length of the small piece 51a in the direction orthogonal to the longitudinal direction of the side wall portion 43 is a length that allows the small pieces 51a adjacent in the direction orthogonal to the longitudinal direction to be arranged on the side wall portion 43 with a 0.3 mm to 0.5 mm distance from each of the end on the inner wall portion 41 side of the side wall portion 43 and the end on the bent portion 43a side. Preferably, the edge of the small piece 51a is chamfered to be round.

The second reinforcing member 52A includes two lines of a plurality of small pieces 52a arranged in the longitudinal direction of the side wall portion 43. The two lines are aligned in the direction in which the inner wall portion 41 faces the outer wall portion 42. Namely, the second reinforcing member 52A has the same configuration as the first reinforcing member 51A in the present modification.

Like the above-described bag-shaped structure 32, when used in the cuff 12, the bag-shaped structure 32A configured as described above can suppress expansion of the side wall portion 43 and improve the vascular compression property while keeping shape followability to the wrist 100 even when the cuff width is reduced. In addition, the bag-shaped structure 32A has a higher expansion property and a higher folding property upon inflation and deflation because the first reinforcing member 51A and second reinforcing member 52A are each arranged by being divided in the direction in which the inner wall portion 41 faces the outer wall portion 42. Accordingly, the bag-shaped structure 32A can achieve closer contact with the wrist 100 and attain high blood pressure measurement accuracy.

[Second Modification]

As shown in FIG. 10, the bag-shaped structure 32B according to the second modification includes an inner wall portion 41, an outer wall portion 42, a pair of side wall portions 43, and a reinforcing member 44B provided on each of the pair of side wall portions 43. The bag-shaped structure 32B also includes a junction 45 and a connection tube 46, although they are omitted in FIG. 10.

The reinforcing member 44B is made of the same material as that of reinforcing member 44. The reinforcing member 44B has shape followability in the direction of wrapping around the wrist 100 as it is divided in the wrapping direction. The thickness of the reinforcing member 44B is in the range from 0.01 mm to 1.00 mm.

As shown in FIG. 10, the reinforcing member 44B includes a first reinforcing member 51B provided on the inner wall portion 41 side with respect to the bent portion 43a of the side wall portion 43, and a second reinforcing member 52 provided on the outer wall portion 42 side with respect to the bent portion 43a.

The first reinforcing member 51B includes a plurality of small pieces 51a arranged in the longitudinal direction of the side wall portion 43. The small piece 51a is a rectangular thin plate made of a resin material. The small piece 51a is fixed to the outer surface of the side wall portion 43 by an adhesive or the like.

The small pieces 51a are set so that the gap between adjacent small pieces 51a is larger than the thickness of the small piece 51a and equal to or smaller than 2 mm. This is because, if the width of the gap is smaller than the thickness of the small piece 51a, the small pieces 51a interfere with each other, and if the width exceeds the upper limit value, the side wall portion 43 between small pieces 51a may expand by the inflation pressure in the air chamber of the bag-shaped structure 32.

For example, the length of the small piece 51a in the longitudinal direction of the side wall portion 43 is 9 mm. In addition, for example, the length of the small piece 51a in the direction orthogonal to the longitudinal direction of the side wall portion 43 is a length that allows the small piece 51a to be arranged on the side wall portion 43 with a 0.3 mm to 0.5 mm distance from each of the end on the inner wall portion 41 side of the side wall portion 43 and the end on the bent portion 43a side. Preferably, the edge of the small piece 51a is chamfered to be round.

The second reinforcing member 52 includes a plurality of small pieces 52a arranged in the longitudinal direction of the side wall portion 43. The small piece 52a is a rectangular thin plate longer in the longitudinal direction of the side wall portion 43 than the small piece 52a used for the first reinforcing member 52B. Since the longitudinal length of the small piece 52a of the second reinforcing member 52 is long, the number of small pieces 52a is smaller than that of small pieces 51a of the first reinforcing member 51B. For example, the length of the small piece 52a in the longitudinal direction of the side wall portion 43 is 10 mm. In other words, the first reinforcing member 51A is divided into a larger number of small pieces 51a than the second reinforcing member 52.

Namely, the reinforcing member 44B has a larger number of small pieces 51a having a shorter length in the longitudinal direction of the side wall portion 43 than the above-described first reinforcing member 51 of reinforcing member 44.

Like the above-described bag-shaped structure 32, when used in the cuff 12, the bag-shaped structure 32B configured as described above can suppress expansion of the side wall portion 43 and improve the vascular compression property while keeping shape followability to the wrist 100 even when the cuff width is reduced.

In addition, in the bag-shaped structure 32B, the first reinforcing member 51B on the inner wall portion 41 side which comes into contact with the wrist 100 is smaller than the second reinforcing member 52 on the base 31 side; therefore, the first reinforcing member 51B is divided into a larger number of small pieces 51a than the second reinforcing member 52. In the bag-shaped structure 32B, the curvature radius on the wrist 100 side is smaller than that on the base 31 side when the bag-shaped structure 32B is wrapped around the wrist 100. Therefore, higher shape followability can be given to the wrist 100 side with a small curvature radius by making the small piece 51a of the first reinforcing member 51B shorter in the longitudinal direction of the side wall portion 43 than the small piece 52a of the second reinforcing member 52. As result, the bag-shaped structure 32B can achieve higher shape followability to the shape of the wrist 100 and closer contact with the wrist 100, and attain high blood pressure measurement accuracy.

[Third Modification]

As shown in FIG. 11, the bag-shaped structure 32C according to the third modification includes an inner wall portion 41, an outer wall portion 42, a pair of side wall portions 43, and a reinforcing member 44C provided on each of the pair of side wall portions 43. The bag-shaped structure 32C also includes a junction 45 and a connection tube 46, although they are omitted in FIG. 11.

The reinforcing member 44C is made of the same material as that of reinforcing member 44. The reinforcing member 44C has shape followability in the direction of wrapping around the wrist 100 as it is provided with flexibility. The thickness of the reinforcing member 44C is in the range from 0.01 mm to 1.00 mm.

As shown in FIG. 11, the reinforcing member 44C includes a first reinforcing member 51C provided on the inner wall portion 41 side with respect to the bent portion 43a of the side wall portion 43, and a second reinforcing member 52C provided on the outer wall portion 42 side with respect to the bent portion 43a.

The first reinforcing member 51C is meshed, and has a rectangular shape extending in the longitudinal direction of the side wall portion 43. The first reinforcing member 51C has high flexibility as it is meshed. The first reinforcing member 51C is fixed to the outer surface of the side wall portion 43 by an adhesive or the like. The length of the first reinforcing member 51C in the direction orthogonal to the longitudinal direction of the side wall portion 43 is a length that allows the first reinforcing member 51C to be arranged on the side wall portion 43 with a 0.3 mm to 0.5 mm distance from each of the end on the inner wall portion 41 side of the side wall portion 43 and the end on the bent portion 43a side.

The second reinforcing member 52C is meshed, and has a rectangular shape extending in the longitudinal direction of the side wall portion 43. Namely, the second reinforcing member 52C has the same configuration as the first reinforcing member 51C in the present modification.

Like the above-described bag-shaped structure 32, when used in the cuff 12, the bag-shaped structure 32C configured as described above can suppress expansion of the side wall portion 43 and improve the vascular compression property while keeping shape followability to the wrist 100 even when the cuff width is reduced.

In addition, in the bag-shaped structure 32C, a pair of reinforcing members 44C, one of which includes one meshed first reinforcing member 51C and the other of which includes one meshed second reinforcing member 52C, are provided on each of the pair of side wall portions 43. Therefore, productivity of the bag-shaped structure 32C is increased because application of an adhesive and registration of the first reinforcing member 51C and the second reinforcing member 52C can be easily performed when the first reinforcing member 51C and the second reinforcing member 52C are fixed to the side wall portion 43.

[Fourth Modification]

As shown in FIG. 12, the bag-shaped structure 32D according to the fourth modification includes an inner wall portion 41, an outer wall portion 42, a pair of side wall portions 43, and a reinforcing member 44D provided on each of the pair of side wall portions 43. The bag-shaped structure 32D also includes a junction 45 and a connection tube 46, although they are omitted in FIG. 12.

The reinforcing member 44D is made of the same material as that of reinforcing member 44C. The reinforcing member 44D has shape followability in the direction of wrapping around the wrist 100 as it is provided with flexibility and divided in the wrapping direction. The thickness of the reinforcing member 44D is in the range from 0.01 mm to 1.00 mm.

As shown in FIG. 12, the reinforcing member 44D includes a first reinforcing member 51D provided on the inner wall portion 41 side with respect to the bent portion 43a of the side wall portion 43, and a second reinforcing member 52D provided on the outer wall portion 42 side with respect to the bent portion 43a.

The first reinforcing member 51D is meshed and includes a plurality of small pieces 51a arranged in the longitudinal direction of the side wall portion 43. The small piece 51a is a rectangular thin plate, and has flexibility as it is meshed. The first reinforcing member 51D is fixed to the outer surface of the side wall portion 43 by an adhesive or the like. The small pieces 51a are set so that the gap between adjacent small pieces 51a is larger than the thickness of the small piece 51a and equal to or smaller than 2 mm. The length of the small piece 51a in the longitudinal direction of the side wall portion 43 is 10 mm. In addition, for example, the length of the small piece 51a in the direction orthogonal to the longitudinal direction of the side wall portion 43 is a length that allows the small piece 51a to be arranged on the side wall portion 43 with a 0.3 mm to 0.5 mm distance from each of the end on the inner wall portion 41 side of the side wall portion 43 and the end on the bent portion 43a side. Preferably, the edge of the small piece 51a is chamfered to be round.

The second reinforcing member 52D is meshed and includes a plurality of small pieces 52a arranged in the longitudinal direction of the side wall portion 43. Namely, the second reinforcing member 52D has the same configuration as the first reinforcing member 51D in the present modification.

Like the above-described bag-shaped structure 32, when used in the cuff 12, the bag-shaped structure 32D configured as described above can suppress expansion of the side wall portion 43 and improve the vascular compression property while keeping shape followability to the wrist 100 even when the cuff width is reduced.

In addition, in the bag-shaped structure 32D, a plurality of small pieces 51a and 52a constituting the first reinforcing member 51D and the second reinforcing member 52D are meshed; therefore, the first reinforcing member 51D and the second reinforcing member 52D have high flexibility. As a result, the bag-shaped structure 32D has improved shape followability to the wrist 100, and can achieve closer contact with the wrist 100 as it has improved bending property in the direction (width direction) orthogonal to the longitudinal direction and wrapping direction of the bag-shaped structure 32D.

[Fifth Modification]

As shown in FIG. 13, the bag-shaped structure 32E according to the fifth modification includes an inner wall portion 41, an outer wall portion 42, a pair of side wall portions 43, and a reinforcing member 44E provided on each of the pair of side wall portions 43. The bag-shaped structure 32E also includes a junction 45 and a connection tube 46, although they are omitted in FIG. 13.

The reinforcing member 44E is made of the same material as that of reinforcing member 44. The reinforcing member 44E has shape followability in the direction of wrapping around the wrist 100 as it is divided in the wrapping direction. The thickness of the reinforcing member 44E is in the range from 0.01 mm to 1.00 mm.

As shown in FIG. 13, the reinforcing member 44E includes a first reinforcing member 51E provided on the inner wall portion 41 side with respect to the bent portion 43a of the side wall portion 43, and a second reinforcing member 52E provided on the outer wall portion 42 side with respect to the bent portion 43a.

The first reinforcing member 51E includes a plurality of small pieces 51a arranged in the longitudinal direction of the side wall portion 43. The small piece 51a is an oval thin plate made of a resin material. The small piece 51a is fixed to the outer surface of the side wall portion 43 by an adhesive or the like.

The small pieces 51a are set so that the gap between adjacent small pieces 51a is larger than the thickness of the small piece 51a and equal to or smaller than 2 mm. For example, the length of the small piece 51a in the longitudinal direction of the side wall portion 43 is 10 mm. In addition, for example, the length of the small piece 51a in the direction orthogonal to the longitudinal direction of the side wall portion 43 is a length that allows the small piece 51a to be arranged on the side wall portion 43 with a 0.3 mm to 0.5 mm distance from each of the end on the inner wall portion 41 side of the side wall portion 43 and the end on the bent portion 43a side.

Namely, the small piece 51a has an oval shape inscribed in the reinforcing member 44 of the above-described embodiment. Preferably, the edge of the small piece 51a is chamfered to be round.

The second reinforcing member 52 includes a plurality of small pieces 52a arranged in the longitudinal direction of the side wall portion 43. The small piece 52a is an oval thin plate made of a resin material. Namely, the second reinforcing member 52E has the same configuration as the first reinforcing member 51E in the present modification.

Like the above-described bag-shaped structure 32, when used in the cuff 12, the bag-shaped structure 32E configured as described above can suppress expansion of the side wall portion 43 and improve the vascular compression property while keeping shape followability to the wrist 100 even when the cuff width is reduced.

[Sixth Modification]

As shown in FIG. 14, the bag-shaped structure 32F according to the sixth modification includes an inner wall portion 41, an outer wall portion 42, a pair of side wall portions 43, and a reinforcing member 44F provided on each of the pair of side wall portions 43. The bag-shaped structure 32F also includes a junction 45 and a connection tube 46, although they are omitted in FIG. 14.

The reinforcing member 44F is made of the same material as that of reinforcing member 44. The reinforcing member 44F has shape followability in the direction of wrapping around the wrist 100 as it is divided in the wrapping direction. The thickness of the reinforcing member 44F is in the range from 0.01 mm to 1.00 mm.

As shown in FIG. 14, the reinforcing member 44F includes a first reinforcing member 51F provided on the inner wall portion 41 side with respect to the bent portion 43a of the side wall portion 43, and a second reinforcing member 52F provided on the outer wall portion 42 side with respect to the bent portion 43a.

The first reinforcing member 51F includes a plurality of small pieces 51a arranged in the longitudinal direction of the side wall portion 43. The small piece 51a is an odd-shaped thin plate made of a resin material. The odd shape refers to a polygonal shape other than a rectangle, or a shape other than a circle or oval. For example, the small piece 51a is a parallelogram with the sides as viewed in the longitudinal direction of the side wall portion 43 made oblique in the longitudinal direction. The small piece 51a is fixed to the outer surface of the side wall portion 43 by an adhesive or the like. The small piece 51a may be, for example, a triangle.

The small pieces 51a are set so that the gap between adjacent small pieces 51a is larger than the thickness of the small piece 51a and equal to or smaller than 2 mm. In addition, for example, the length of the small piece 51a in the direction orthogonal to the longitudinal direction of the side wall portion 43 is a length that allows the small piece 51a to be arranged on the side wall portion 43 with a 0.3 mm to 0.5 mm distance from each of the end on the inner wall portion 41 side of the side wall portion 43 and the end on the bent portion 43a side. Preferably, the edge of the small piece 51a is chamfered to be round.

The second reinforcing member 52F includes a plurality of small pieces 52a arranged in the longitudinal direction of the side wall portion 43. The small piece 52a is an odd-shaped thin plate made of a resin material. Namely, the second reinforcing member 52E has the same configuration as the first reinforcing member 51E in the present modification. The small pieces 51a in the first reinforcing member 51E are arranged to be mirror images of the small pieces 52a in the second reinforcing member 52E with respect to the bent portion 43a of the side wall portion 43.

Like the above-described bag-shaped structure 32, when used in the cuff 12, the bag-shaped structure 32F configured as described above can suppress expansion of the side wall portion 43 and improve the vascular compression property while keeping shape followability to the wrist 100 even when the cuff width is reduced.

[Seventh Modification]

As shown in FIG. 15, the bag-shaped structure 32G according to the seventh modification includes an inner wall portion 41, an outer wall portion 42, a pair of side wall portions 43, and a reinforcing member 44G provided on each of the pair of side wall portions 43. The bag-shaped structure 32G also includes a junction 45 and a connection tube 46, although they are omitted in FIG. 15.

The reinforcing member 44G is made of the same material as that of reinforcing member 44. The reinforcing member 44G has shape followability in the direction of wrapping around the wrist 100 as it is partly divided in the wrapping direction. The thickness of the reinforcing member 44G is in the range from 0.01 mm to 1.00 mm.

The reinforcing member 44G includes a first reinforcing member 51G provided on the inner wall portion 41 side with respect to the bent portion 43a of the side wall portion 43, and a second reinforcing member 52G provided on the outer wall portion 42 side with respect to the bent portion 43a.

The first reinforcing member 51G includes a plurality of small pieces 51a arranged in the longitudinal direction of the side wall portion 43 and a plurality of connection portions 51b provided between the small pieces 51a and integrally connecting the small pieces 51a in the direction orthogonal to the longitudinal direction of the side wall portion 43. In the first reinforcing member 51G, a plurality of small pieces 51a and a plurality of connection portions 51b are integrally formed at the time of molding. The first reinforcing member 51G is produced by integrally molding a plurality of small pieces 51a and a plurality of connection portions 51b by use of a resin material. The first reinforcing member 51G is fixed to the outer surface of the side wall portion 43 by an adhesive or the like.

The small piece 51a is a rectangular thin plate. The small pieces 51a are set so that the gap between adjacent small pieces 51a is larger than the thickness of the small piece 51a and equal to or smaller than 2 mm. This is because, if the width of the gap is smaller than the thickness of the small piece 51a, the small pieces 51a interfere with each other, and if the width exceeds the upper limit value, the side wall portion 43 between small pieces 51a may expand by the inflation pressure in the air chamber of the bag-shaped structure 32.

For example, the length of the small piece 51a in the longitudinal direction of the side wall portion 43 is 10 mm. In addition, for example, the length of the small piece 51a in the direction orthogonal to the longitudinal direction of the side wall portion 43 is a length that allows the small piece 51a to be arranged on the side wall portion 43 with a 0.3 mm to 0.5 mm distance from each of the end on the inner wall portion 41 side of the side wall portion 43 and the end on the bent portion 43a side. Preferably, the edge of the small piece 51a is chamfered to be round.

The connection portions 51b are provided on the inner wall portion 41 side of the small pieces 51a as viewed in the direction orthogonal to the longitudinal direction of the side wall portion 43. In other words, the connection portions 51b integrally connect adjacent small pieces 51a with each other on the wrist 100 side with the reinforcing member 44G fixed to the side wall portion 43. For example, the connection portion 51b has a width in the range from 0.2 mm to 0.4 mm in the direction orthogonal to the longitudinal direction of the side wall portion 43. This is to prevent the shape followability provided by the small pieces 51a from being lowered and not to inhibit the change of the shape of the side wall portion 43 when the bag-shaped structure 32G is wrapped around the wrist 100. Since the first reinforcing member 51G has the same configuration as the first reinforcing member 51 of the above-described embodiment if the connection portions 51b are cut after the first reinforcing member 51G is fixed to the side wall portion 43, the connection portions 51b may have a size and shape which may cause cutting of the connection portions 51b.

The second reinforcing member 52G includes a plurality of small pieces 52a arranged in the longitudinal direction of the side wall portion 43 and a plurality of connection portions 52b provided between the small pieces 52a and integrally connecting the small pieces 52a in the direction orthogonal to the longitudinal direction of the side wall portion 43. The small pieces 52a and connection portions 52b of the second reinforcing member 52G are integrally formed in molding. The second reinforcing member 52G is fixed to the outer surface of the side wall portion 43 by an adhesive or the like.

The small piece 52a is a rectangular thin plate made of a resin material. The small pieces 52a are set so that the gap between adjacent small pieces 52a is larger than the thickness of the small piece 52a and equal to or smaller than 2 mm. The reason therefor is the same as that for the small pieces 51a of the first reinforcing member 51G. For example, the length of the small piece 52a in the longitudinal direction of the side wall portion 43 is 10 mm. In addition, for example, the length of the small piece 52a in the direction orthogonal to the longitudinal direction of the side wall portion 43 is a length that allows the small piece 52a to be arranged on the side wall portion 43 with a 0.3 mm to 0.5 mm distance from each of the end on the outer wall portion 42 side of the side wall portion 43 and the end on the bent portion 43a side. Preferably, the edge of the small piece 52a is chamfered to be round.

The connection portions 52b are provided on the inner wall portion 41 side with respect to the small pieces 52a as viewed in the direction orthogonal to the longitudinal direction of the side wall portion 43. In other words, the connection portions 52b integrally connect adjacent small pieces 52a with each other on the wrist 100 side with the reinforcing member 44G fixed to the side wall portion 43. For example, the connection portion 52b has a width in the range from 0.2 mm to 0.4 mm in the direction orthogonal to the longitudinal direction of the side wall portion 43. This is to prevent the shape followability provided by the small pieces 52a from being lowered and not to inhibit the change of the shape of the side wall portion 43 when the bag-shaped structure 32G is wrapped around the wrist 100, as described above as to the connection portion 51b. Since the second reinforcing member 52G has the same configuration as the second reinforcing member 52 of the above-described embodiment if the connection portions 52b are cut after the second reinforcing member 52G is fixed to the side wall portion 43, the connection portions 52b may have a size and shape which may cause cutting of the connection portions 52b. Namely, the second reinforcing member 52E has the same configuration as the first reinforcing member 51E in the present modification.

Such a first reinforcing member 51G and second reinforcing member 52G have a configuration in which the ends of the small pieces 51a and 52a positioned on the small curvature radius side when the bag-shaped structure 32 is wrapped around the wrist 100 are connected by the connection portions 51b and 52b.

Like the above-described bag-shaped structure 32, when used in the cuff 12, the bag-shaped structure 32G configured as described above can suppress expansion of the side wall portion 43 and improve the vascular compression property while keeping shape followability to the wrist 100 even when the cuff width is reduced. In addition, the bag-shaped structure 32G has a configuration in which the first reinforcing member 51G and second reinforcing member 52G are substantially divided into a plurality of small pieces 51a and 52b to attain shape followability, and the adjacent small pieces 51a and 52a are connected to each other by a plurality of connection portions 51b and 52b. Therefore, each of the first reinforcing member 51G and the second reinforcing member 52G is an integrally-molded item, and productivity of the bag-shaped structure 32G is increased because application of an adhesive and registration of the first reinforcing member 51G and the second reinforcing member 52G can be easily performed when the first reinforcing member 51G and the second reinforcing member 52G are fixed to the side wall portion 43.

[Eighth Modification]

As shown in FIG. 16, the bag-shaped structure 32H according to the eighth modification includes an inner wall portion 41, an outer wall portion 42, a pair of side wall portions 43, and a reinforcing member 44H provided on each of the pair of side wall portions 43. The bag-shaped structure 32H also includes a junction 45 and a connection tube 46, although they are omitted in FIG. 16.

The reinforcing member 44H is made of the same material as that of reinforcing member 44. The reinforcing member 44H has shape followability in the direction of wrapping around the wrist 100 as it is partly divided in the wrapping direction. The thickness of the reinforcing member 44H is in the range from 0.01 mm to 1.00 mm.

The reinforcing member 44H includes a plurality of small pieces 53 arranged continuously from the inner wall portion 41 side to the outer wall portion 42 side of the side wall portion 43 in the longitudinal direction of the side wall portion 43. The small piece 53 is a rectangular thin plate made of a resin material, and has a perforation 53a extending along the bent portion 43a of the side wall portion 43. The perforation 53a is constituted by a plurality of small holes 53b aligned in one direction at predetermined intervals. The small holes 53b are provided in the small piece 53 with a pitch in the range from 0.4 mm to 0.5 mm. The small piece 53 is fixed to the outer surface of the side wall portion 43 by an adhesive or the like.

The small pieces 53 are set so that the gap between adjacent small pieces 53 is larger than the thickness of the small piece 53 and equal to or smaller than 2 mm. In addition, for example, the length of the small piece 53 in the direction orthogonal to the longitudinal direction of the side wall portion 43 is a length that allows the small piece 53 to be arranged on the side wall portion 43 with a 0.3 mm to 0.5 mm distance from each of the end on the inner wall portion 41 side of the side wall portion 43 and the end on the outer wall portion 42 side. Preferably, the edge of the small piece 53 is chamfered to be round.

The small piece 53 fixed to the side wall portion 43 is configured to be bent along the perforation 53a when the side wall portion 43 is folded along the bent portion 43a.

Like the above-described bag-shaped structure 32, when used in the cuff 12, the bag-shaped structure 32H configured as described above can suppress expansion of the side wall portion 43 and improve the vascular compression property while keeping shape followability to the wrist 100 even when the cuff width is reduced.

In addition, in the bag-shaped structure 32G, the reinforcing member 44H has a configuration in which the small pieces 53 each having the perforation 53a along the bent portion 43a are arranged in the longitudinal direction of the side wall portion 43. Therefore, the reinforcing member 44H needs to have only the small pieces 53 arranged in the longitudinal direction of the side wall portion 43, and the number of small pieces 53 can be reduced. As a result, application of an adhesive and registration of small pieces 53 are easily performed when the reinforcing member 44 is fixed to the side wall portion 43, and high productivity can be achieved.

Since the small pieces 53 are bent along the perforation 53a, the small pieces 53 do not reduce the folding property at the bent portion 43a of the side wall portion 43; therefore, when the bag-shaped structure 32H inflates or deflates, the small pieces 53 do not inhibit the inflation or deflation. Even if the small pieces 53 are split along the perforations 53*a* by repeated inflation and deflation, the resultant configuration is the same as that of the first reinforcing member 51 and the second reinforcing member 52 of the above-described embodiment, and the bag-shaped structure 32H produces the same effect as the bag-shaped structure 32 of the embodiment.

[Ninth Modification]

As shown in FIG. 17, the bag-shaped structure 32I according to the ninth modification includes an inner wall portion 41, an outer wall portion 42, a pair of side wall portions 43I, and a reinforcing member 44 provided on each of the pair of side wall portions 43I. The bag-shaped structure 32I also includes a junction 45 and a connection tube 46, although they are omitted in FIG. 17.

The side wall portion 43I is a flat plane continuous with the inner wall portion 41 and the outer wall portion 42, and includes a folding portion 43I*a* to bend the side wall portion 43I toward the internal space of the bag-shaped structure 32H in approximately the middle in the direction in which the inner wall portion 41 faces the outer wall portion 42. The folding portion 43I*a* is constituted by, for example, a recess or the like partly provided when molding the sheet member.

Like the above-described bag-shaped structure 32, when used in the cuff 12, the bag-shaped structure 32I configured as described above can suppress expansion of the side wall portion 43 and improve the vascular compression property while keeping shape followability to the wrist 100 even when the cuff width is reduced.

In the bag-shaped structure 32I, the side wall portion 43I need not be bent toward the internal space of the bag-shaped structure 32I in advance, and may be a planer side wall portion 43I. The reinforcing member 44 has a configuration in which the first reinforcing member 51 and second reinforcing member 52 constituted by a plurality of small pieces 51*a* and 52*a* are provided on the side wall portion 43I on the inner wall portion 41 side and the outer wall portion 42 side, respectively, with the folding portion 43I*a* of the side wall portion 43I interposed therebetween. Therefore, the folding portion 43I*a* is arranged in the gap between the first reinforcing member 51 and the second reinforcing member 52, and can prevent the side wall portion 43I from being folded at a portion other than the folding portion 43I*a*. As a result, the bag-shaped structure 32I can have a planer side wall portion 43I, and can be easily manufactured.

[Tenth Modification]

As shown in FIG. 18, the bag-shaped structure 32J according to the tenth modification includes an inner wall portion 41, an outer wall portion 42, a pair of side wall portions 43J, and a reinforcing member 44 and junction 45 provided on each of the pair of side wall portions 43J. The bag-shaped structure 32J also includes a connection tube 46, although it is omitted in FIG. 18.

The pair of side wall portions 43J has a multi-tier structure in which multiple pairs of side wall portions 43 are provided in the direction in which the inner wall portion 41 faces the outer wall portion 42. For example, in the pair of side wall portions 43J, two side wall portions 43 are integrally arranged in the direction in which the inner wall portion 41 faces the outer wall portion 42. The reinforcing member 44 and the junction 45 are provided for each of the two side wall portions 43.

Like the above-described bag-shaped structure 32, when used in the cuff 12, the bag-shaped structure 32J configured as described above can suppress expansion of the side wall portion 43 and improve the vascular compression property while keeping shape followability to the wrist 100 even when the cuff width is reduced.

In addition, since the side wall portion 43J is bent to the internal space at a plurality of positions, the bag-shaped structure 32J is apt to inflate in a direction that compresses the wrist 100, and easily follows the shape of the living body; therefore, the bag-shaped structure 32J can attain high blood pressure measurement accuracy even when the cuff width is reduced. In addition, the bag-shaped structure 32J has an increased bellows effect.

[Eleventh Modification]

As shown in FIG. 19, the bag-shaped structure 32K according to the tenth modification includes an inner wall portion 41, an outer wall portion 42, a pair of side wall portions 43, a reinforcing member 44 and junction 45 provided on each of the pair of side wall portions 43. In other words, the bag-shaped structure 32K includes two bag-shaped structures 32 joined by joining the inner wall portion 41 of one bag-shaped structure 32 to the outer wall portion 42 of the other bag-shaped structure 32, and a communication hole 47 that allows the two bag-shaped structures 32 to fluidly communicate with each other in the joined inner wall portion 41 and outer wall portion 42. The bag-shaped structure 32K also includes a connection tube 46 in one of the two bag-shaped structures 32, although it is omitted in FIG. 19.

Like the above-described bag-shaped structure 32, when used in the cuff 12, the bag-shaped structure 32K configured as described above can provide high blood pressure measurement accuracy even when the cuff width is reduced. Furthermore, in the bag-shaped structure 32K, the two bag-shaped structures 32 are joined together, and the internal spaces of the two bag-shaped structures 32 fluidly communicate with each other by the communication hole 47.

Therefore, like the above-described bag-shaped structure 32, when used in the cuff 12, the bag-shaped structure 32K can suppress expansion of the side wall portion 43 and improve the vascular compression property while keeping shape followability to the wrist 100 even when the cuff width is reduced.

In addition, since the two bag-shaped structures 32 each inflate in the direction that compresses the wrist 100, the bag-shaped structure 32K can easily follow the living body shape, and attain high blood pressure measurement accuracy even when the cuff width is reduced. In addition, the bag-shaped structure 32K has an increased bellows effect.

Figure 20:
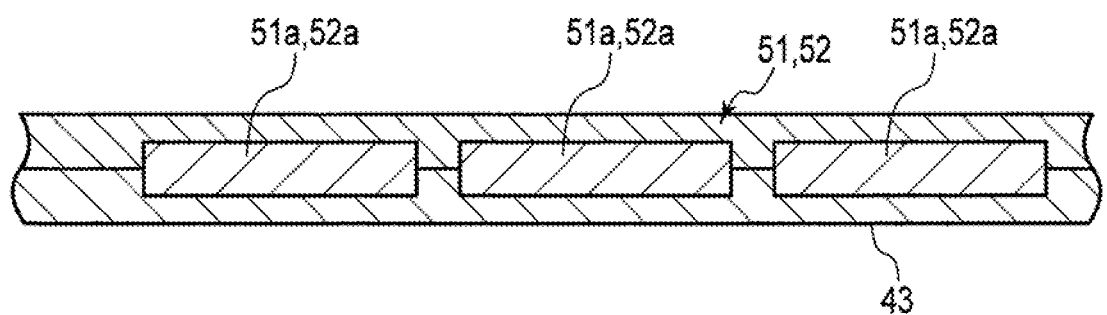
FIG. 20 is a cross-sectional view showing configurations of a side wall portion and reinforcing member of a bag-shaped structure according to another example of the present invention.

The present invention is not limited to the above-described embodiment and modifications. For example, described above is the configuration in which the reinforcing member 44 of the bag-shaped structure 32 is fixed to the outer surface of the side wall portion 43 by an adhesive; however, the configuration is not limited to this. For example, as shown by the side wall portion 43 and reinforcing member 44 of the bag-shaped structure 32 according to another example shown in FIG. 20, the small pieces 51*a* and 52*a* constituting the reinforcing member 44 may be provided inside the side wall portion 43. Such a bag-shaped structure 32 can be manufactured by performing insert molding so that the small pieces 51*a* and 52*a* are arranged in the sheet member.

Of course, the above-described reinforcing members other than reinforcing member 44 may be inserted in the side wall portion 43.

The bag-shaped structure 32 may have another configuration as long as the reinforcing member 44 provided to the side wall portion 43 is divided in the wrapping direction or has flexibility so that the bag-shaped structure 32 has shape followability to the wrist 100. For example, configurations of the above embodiment and modifications may be combined, such as using, for the first reinforcing member, the configuration of one of the above embodiment and modifications and using, for the second reinforcing member, the configuration of another one of the above embodiment and modifications which is different from that of the first reinforcing member.

Furthermore, the bag-shaped structure 32 may have a configuration in which the second moment of area is increased or decreased as appropriate by making the thickness of each portion such as the corner of the outer wall portion 42 and the side wall portion 43, or the distal end of the side wall portion 43 different from the thicknesses of the other portions, or a configuration in which a portion in a shape that improves, for example, the folding property of the side wall portions 43 is provided.

The above-described bag-shaped structure 32D has a configuration in which the first reinforcing member 51D on the inner wall portion 41 side and the second reinforcing member 52D on the outer wall portion 42 side are a plurality of meshed small pieces 51a and 52a; however, the configuration is not limited to this. For example, the bag-shaped structure may include a first reinforcing member 51D constituted by a plurality of meshed small pieces 51a on the inner wall portion 41 side having a small curvature radius when the bag-shaped structure is wrapped around the wrist 100, and a non-divided second reinforcing member 52C on the outer wall portion 42 side.

The above-described bag-shaped structure 32G has a configuration in which the reinforcing members 51G and 52G are respectively formed by molded items in which a plurality of small pieces 51a and 52a arranged in the longitudinal direction of the side wall portion 43 are integrally connected by the connection portions 51b and 52b. For example, the reinforcing member may have a configuration in which a plurality of molded items each formed by integrating two adjacent small pieces by a connection portion are arranged in the longitudinal direction of the side wall portion 43, or a configuration in which three adjacent small pieces are integrated by two connection portions.

Namely, the present invention is not limited to the above-described embodiments, and can be modified in practice, without departing from the gist of the invention. In addition, embodiments may be combined as appropriate where possible, in which case a combined advantage can be attained. Furthermore, the above-described embodiments include various stages of the invention, and various inventions can be extracted by suitably combining the structural elements disclosed herein. For example, even if some structural elements of all the structural elements disclosed in the embodiments are deleted, the embodiment from which those structural elements are deleted can be extracted as an invention as long as the problem to be solved by the invention can be solved, and the advantages of the invention can be attained.

EXAMPLES

In order to concretize the features of the present invention, examples and evaluation tests will be described below. However, the scope of the present invention is not limited to the following examples. In the following examples 1 to 10 and comparative examples 1 and 2, the width H of the bag-shaped structure was 27 mm.

Example 1

A bag-shaped structure 32 according to the embodiment was prepared. Regarding the material of the inner wall portion 41, the outer wall portion 42, and the side wall portion 43, a silicone material having a Shore A hardness of 25 was used as a thermoplastic elastomer. The thickness of the inner wall portion 41, the outer wall portion 42, and the side wall portion 43 was 0.15 mm. As the material of the reinforcing member 44, polyethylene terephthalate resin was used. The thickness of the reinforcing member 44 was 0.10 mm. The length of the small pieces 51a and 52a of the reinforcing member 44 in the longitudinal direction of the side wall portion 43 was 10 mm. The small pieces 51a and 52a had a shape which allows the small pieces 51a and 52a to be arranged with a 0.3 mm to 0.5 mm distance from each of the end on the inner wall portion 41 side of the side wall portion 43 and the bent portion 43a, and each of the end on the outer wall portion 42 side and the bent portion 43a, respectively. The small pieces 51a and 52a were fixed to the side wall portion 43 by an adhesive so that the interval between small pieces 51a and that between small pieces 52a are in the range from 0.2 mm to 0.5 mm.

Example 2

A bag-shaped structure 32A according to the first modification was prepared. Regarding the material of the inner wall portion 41, the outer wall portion 42, and the side wall portion 43, a silicone material having a Shore A hardness of 25 was used as a thermoplastic elastomer. The thickness of the inner wall portion 41, the outer wall portion 42, and the side wall portion 43 was 0.15 mm. As the material of the reinforcing member 44A, polyethylene terephthalate resin was used. The thickness of the reinforcing member 44A was 0.10 mm. The length of the small pieces 51a and 52a of the reinforcing member 44A in the longitudinal direction of the side wall portion 43 was 10 mm. The reinforcing member 44A had a shape which allows (i) the end on the inner wall portion 41 side of the side wall portion 43 and the small pieces 51a of one line, (ii) the small pieces 51a of one line and those of the other line, (iii) the small pieces 51a of the other line and the bent portion 43a, (iv) the end on the outer wall portion 42 side and the small pieces 52a of one line, (v) the small pieces 52a of one line and those of the other line, and (vi) the small pieces 52a of the other line and the bent portion 43a, to be arranged with a 0.3 mm to 0.5 mm distance from each other. The small pieces 51a and 52a were fixed to the side wall portion 43 by an adhesive so that the interval between small pieces 51a and that between small pieces 52a are in the range from 0.2 mm to 0.5 mm.

Example 3

A bag-shaped structure 32B according to the second modification was prepared. Regarding the material of the inner wall portion 41, the outer wall portion 42, and the side wall portion 43, a silicone material having a Shore A hardness of 25 was used as a thermoplastic elastomer. The thickness of the inner wall portion 41, the outer wall portion 42, and the side wall portion 43 was 0.15 mm. As the material of the reinforcing member 44B, polyethylene terephthalate resin was used. The thickness of the reinforcing member 44B was 0.10 mm. The length of the small pieces 51a of the reinforcing member 44B in the longitudinal direction of the side wall portion 43 was 10 mm, and that of the small pieces 52a was 9 mm. The small pieces 51a and 52a had a shape which allows the small pieces 51a and 52a to be arranged with a 0.3 mm to 0.5 mm distance from each of the end on the inner wall portion 41 side of the side wall portion 43 and the bent portion 43a, and each of the end on the outer wall portion 42 side and the bent portion 43a, respectively. The small pieces 51a and 52a were fixed to the side wall portion 43 by an adhesive so that the interval between small pieces 51a and that between small pieces 52a are in the range from 0.2 mm to 0.5 mm.

Example 4

A bag-shaped structure 32C according to the third modification was prepared. Regarding the material of the inner wall portion 41, the outer wall portion 42, and the side wall portion 43, a silicone material having a Shore A hardness of 25 was used as a thermoplastic elastomer. The thickness of the inner wall portion 41, the outer wall portion 42, and the side wall portion 43 was 0.15 mm. As the material of the reinforcing member 44C, polypropylene resin was used. The thickness of the reinforcing member 44C was 0.25 mm. The first reinforcing member 51C and the second reinforcing member 52C were a mesh with a mesh size of #100. The first reinforcing member 51C and the second reinforcing member 52C had a shape that allows the first reinforcing member 51C and the second reinforcing member 52C to be arranged with a 0.3 mm to 0.5 mm distance from each of the end on the inner wall portion 41 side of the side wall portion 43 and the bent portion 43a, and each of the end on the outer wall portion 42 side and the bent portion 43a, respectively, and were fixed to the side wall portion 43 by an adhesive.

Example 5

A bag-shaped structure 32D according to the fourth modification was prepared. Regarding the material of the inner wall portion 41, the outer wall portion 42, and the side wall portion 43, a silicone material having a Shore A hardness of 25 was used as a thermoplastic elastomer. The thickness of the inner wall portion 41, the outer wall portion 42, and the side wall portion 43 was 0.15 mm. As the material of the reinforcing member 44D, polypropylene resin was used. The thickness of the reinforcing member 44D was 0.25 mm. The length of the small pieces 51a and 52a of the reinforcing member 44D in the longitudinal direction of the side wall portion 43 was 10 mm. The small pieces 51a and 52a had a mesh with a mesh size of #100. The small pieces 51a and 52a had a shape which allows the small pieces 51a and 52a to be arranged with a 0.3 mm to 0.5 mm distance from each of the end on the inner wall portion 41 side of the side wall portion 43 and the bent portion 43a, and each of the end on the outer wall portion 42 side and the bent portion 43a, respectively. The small pieces 51a and 52a were fixed to the side wall portion 43 by an adhesive so that the interval between small pieces 51a and that between small pieces 52a are in the range from 0.2 mm to 0.5 mm.

Example 6

A bag-shaped structure 32E according to the fifth modification was prepared. Regarding the material of the inner wall portion 41, the outer wall portion 42, and the side wall portion 43, a silicone material having a Shore A hardness of 25 was used as a thermoplastic elastomer. The thickness of the inner wall portion 41, the outer wall portion 42, and the side wall portion 43 was 0.15 mm. As the material of the reinforcing member 44E, polyethylene terephthalate resin was used. The thickness of the reinforcing member 44E was 0.10 mm. The length of the small pieces 51a and 52a of the reinforcing member 44E in the longitudinal direction of the side wall portion 43 was 10 mm. The small pieces 51a and 52a had an oval shape that allows the small pieces 51a and 52a to be arranged with a 0.3 mm to 0.5 mm distance from each of the end on the inner wall portion 41 side of the side wall portion 43 and the bent portion 43a, and each of the end on the outer wall portion 42 side and the bent portion 43a, respectively. The small pieces 51a and 52a were fixed to the side wall portion 43 by an adhesive so that the interval between small pieces 51a and that between small pieces 52a are in the range from 0.2 mm to 0.5 mm.

Example 7

A bag-shaped structure 32F according to the sixth modification was prepared. Regarding the material of the inner wall portion 41, the outer wall portion 42, and the side wall portion 43, a silicone material having a Shore A hardness of 25 was used as a thermoplastic elastomer. The thickness of the inner wall portion 41, the outer wall portion 42, and the side wall portion 43 was 0.15 mm. As the material of the reinforcing member 44F, polyethylene terephthalate resin was used. The thickness of the reinforcing member 44F was 0.10 mm. The length of the small pieces 51a and 52a of the reinforcing member 44F in the longitudinal direction of the side wall portion 43 was 10 mm. The small pieces 51a and 52a had a parallelogram shape as a polygonal shape that allows the small pieces 51a and 52a to be arranged with a 0.3 mm to 0.5 mm distance from each of the end on the inner wall portion 41 side of the side wall portion 43 and the bent portion 43a, and each of the end on the outer wall portion 42 side and the bent portion 43a, respectively. The small pieces 51a and 52a were fixed to the side wall portion 43 by an adhesive so that the interval between small pieces 51a and that between small pieces 52a are in the range from 0.2 mm to 0.5 mm.

Example 8

A bag-shaped structure 32G according to the seventh modification was prepared. Regarding the material of the inner wall portion 41, the outer wall portion 42, and the side wall portion 43G, a silicone material having a Shore A hardness of 25 was used as a thermoplastic elastomer. The thickness of the inner wall portion 41, the outer wall portion 42, and the side wall portion 43 was 0.15 mm. As the material of the reinforcing member 44G, polyethylene terephthalate resin was used. The thickness of the reinforcing member 44G was 0.10 mm. The length of the small pieces 51a and 52a of the reinforcing member 44G in the longitudinal direction of the side wall portion 43 was 10 mm. The small pieces 51a and 52a had a shape that allows the small pieces 51a and 52a to be arranged with a 0.3 mm to 0.5 mm distance from each of the end on the inner wall portion 41 side of the side wall portion 43 and the bent portion 43a, and each of the end on the outer wall portion 42 side and the bent portion 43a, respectively. The small pieces 51a and 52a were fixed to the side wall portion 43 by an adhesive so that the interval between small pieces 51a and that between small pieces 52a are in the range from 0.2 mm to 0.5 mm.

Example 9

A bag-shaped structure 32H according to the eighth modification was prepared. Regarding the material of the inner wall portion 41, the outer wall portion 42, and the side wall portion 43, a silicone material having a Shore A hardness of 25 was used as a thermoplastic elastomer. The thickness of the inner wall portion 41, the outer wall portion 42, and the side wall portion 43 was 0.15 mm. As the material of the reinforcing member 44H, polyethylene terephthalate resin was used. The thickness of the reinforcing member 44H was 0.10 mm. The length of the small pieces 51a and 52a of the reinforcing member 44H in the longitudinal direction of the side wall portion 43 was 10 mm. The width of the connection portions 51b and 52b of the reinforcing member 44H in the direction in which the inner wall portion 41 faces the outer wall portion 42 was within the range from 0.2 mm to 0.4 mm. The small pieces 51a and 52a had a shape which allows the small pieces 51a and 52a to be arranged with a 0.3 mm to 0.5 mm distance from each of the end on the inner wall portion 41 side of the side wall portion 43 and the bent portion 43a, and each of the end on the outer wall portion 42 side and the bent portion 43a, respectively. The small pieces 51a and 52a were fixed to the side wall portion 43 by an adhesive so that the interval between small pieces 51a and that between small pieces 52a are in the range from 0.2 mm to 0.5 mm.

Example 10

A bag-shaped structure 321 according to the ninth modification was prepared. Regarding the material of the inner wall portion 41, the outer wall portion 42, and the side wall portion 431, a silicone material having a Shore A hardness of 25 was used as a thermoplastic elastomer. The thickness of the inner wall portion 41, the outer wall portion 42, and the side wall portion 431 was 0.15 mm. As the material of the reinforcing member 44, polyethylene terephthalate resin was used. The thickness of the reinforcing member 44 was 0.10 mm. The length of the small pieces 53 of the reinforcing member 44 in the longitudinal direction of the side wall portion 431 was 10 mm. The small pieces 53 had a shape that allows the small pieces 53 to be arranged with a 0.3 mm to 0.5 mm distance from each of the end on the inner wall portion 41 side of the side wall portion 431 and the end on the outer wall portion 42 side. A plurality of small pieces 51a and 52a were fixed to the side wall portion 431 by an adhesive so that the interval between small pieces 51a and that between small pieces 52a is within the range from 0.2 mm to 0.5 mm.

Comparative Example 1

As Comparative Example 1, a bag-shaped structure having a configuration obtained by excluding the reinforcing member 44 from the bag-shaped structure 32 of Example 1 was prepared. Regarding the material of the inner wall portion 41, the outer wall portion 42, and the side wall portion 43, a silicone material having a Shore A hardness of 25 was used as a thermoplastic elastomer. The thickness of the inner wall portion 41, the outer wall portion 42, and the side wall portion 43 was 0.15 mm.

Comparative Example 2

As Comparative Example 2, a bag-shaped structure having a configuration obtained by modifying the configuration of the bag-shaped structure 32 of Example 1 to include a first reinforcing member and second reinforcing member in which a plurality of small pieces 51a and a plurality of small pieces 52a of the reinforcing member 44 are each integrated, i.e., a bag-shaped structure including a reinforcing member constituted by a non-divided first reinforcing member and second reinforcing member was prepared. Regarding the material of the inner wall portion 41, the outer wall portion 42, and the side wall portion 43, a silicone material having a Shore A hardness of 25 was used as a thermoplastic elastomer. The thickness of the inner wall portion 41, the outer wall portion 42, and the side wall portion 43 was 0.15 mm. As the material of the reinforcing member 44, polypropylene resin was used. The thickness of the reinforcing member 44 was 0.10 mm. The first reinforcing member and the second reinforcing member had a shape that allows the first reinforcing member and the second reinforcing member to be arranged with a 0.3 mm to 0.5 mm distance from each of the end on the inner wall portion 41 side of the side wall portion 43 and the bent portion 43a, and each of the end on the outer wall portion 42 side and the bent portion 43a, respectively, and were fixed to the side wall portion 43 by an adhesive.

[Evaluation Test 1]

For Evaluation Test 1, an inflation evaluation test was performed for the bag-shaped structures of Examples 1 to 10 and Comparative Examples 1 and 2.

In the inflation evaluation test, each bag-shaped structure was inflated three times with the pressure of 300 mmHg, and whether or not the pair of side wall portions 43 expanded was determined by visual evaluation. A bag-shaped structure with both side wall portions 43 not inflated at all was determined as good, and a bag-shaped structure with at least one side wall portion 43 inflated at least once was determined as bad.

[Evaluation Test 2]

For Evaluation Test 2, a vascular compression property evaluation test was performed for the bag-shaped structures of Examples 1 to 10 and Comparative Examples 1 and 2.

In the vascular compression property evaluation test, a blood pressure value of the same person was measured alternately by a wrist blood pressure monitor (blood pressure monitor 1) including the bag-shaped structure prepared according to each of Examples 1 to 10 and Comparative Examples 1 and 2 and a commercially-available upper-arm blood pressure monitor. Measurement of a blood pressure value was performed 10 times in total for each blood pressure monitor.

Here, an upper-arm blood pressure monitor model HEM-7120 manufactured by Omron Healthcare Co., Ltd. was used as the upper-arm blood pressure monitor. The upper-arm blood pressure monitor was attached to the upper arm, and the blood pressure monitors 1 of each of the examples and the comparative examples were attached to the wrist 100.

After that, the standard deviation of the differences between the blood pressure values obtained by the upper-arm blood pressure monitor and the blood pressure values obtained by each wrist blood pressure monitor was obtained.

The standard deviation of the blood pressure values obtained by 10 measurements with the upper-arm blood pressure monitor was approximately 7 mmHg. This standard deviation was defined as a reference value. Therefore, the bag-shaped structure 32 whose standard deviation of the differences between the blood pressure values obtained by the upper-arm blood pressure monitor and those obtained by the wrist blood pressure monitor is less than 7 mmHg was determined as good, i.e., determined as realizing the measurement accuracy equivalent to that of the upper-arm blood pressure monitor. In contrast, the bag-shaped structure 32 whose standard deviation was 7 mmHg or more was determined as having an insufficient vascular compression property, i.e., as failing to realize the measurement accuracy equivalent to that of the upper-arm blood pressure monitor.

[Results of Evaluation Tests]

The results of the Evaluation Tests 1 and 2 are shown in Table 1.

TABLE 1

| | Inflation evaluation Result | Vascular compression property evaluation | |
|---|---|---|---|
| | | Result | Standard deviation value |
| Example 1 | Good | Good | 3 mmHg |
| Example 2 | Good | Good | 3 mmHg |
| Example 3 | Good | Good | 3 mmHg |
| Example 4 | Good | Good | 6 mmHg |
| Example 5 | Good | Good | 4 mmHg |
| Example 6 | Good | Good | 5 mmHg |
| Example 7 | Good | Good | 5 mmHg |
| Example 8 | Good | Good | 5 mmHg |
| Example 9 | Good | Good | 3 mmHg |
| Example 10 | Good | Good | 3 mmHg |
| Comparative example 1 | Bad | Bad | 26 mmHg |
| Comparative example 2 | Good | Bad | Could not be measured |

As shown in Table 1, Examples 1 to 10 showed good results both in the evaluation of expansion of the side wall portion 43 in Evaluation Test 1 and the evaluation of the vascular compression property in Evaluation Test 2.

In Example 4, the pair of first reinforcing members 51C and pair of second reinforcing members 52C provided on the pair of side wall portions 43 are meshed, but not divided; therefore, Example 4 showed a slightly larger standard deviation value than the other examples, but the standard deviation value satisfied the reference for good results as an evaluation result.

Comparative Example 1 showed a bad result with the standard deviation value of 26 mmHg, which is considered to be caused because the inflation pressure was lost at both side wall portions 43, and the vascular compression property was thereby lowered. In Comparative Example 2, the standard deviation value could not be measured. This is considered to be caused because the configuration of Comparative Example 2 includes a non-divided reinforcing member in a thin plate shape; therefore, the reinforcing member inhibited the change of the shape of the bag-shaped structure, the bag-shaped structure accordingly failed to have shape followability to the wrist 100, and the reinforcing member inhibited the bag-shaped structure from coming into close contact with the wrist 100.

Those results showed that, to reinforce, with the reinforcing member 44, the side wall portion 43 of the bag-shaped structure 32 used in the cuff 12 of the blood pressure monitor 1 for attaining high blood pressure measurement accuracy, the reinforcing member 44 needs to be divided in the wrapping direction or have high flexibility.

Those results also showed that, if the bag-shaped structure 32 used in the cuff 12 of the blood pressure monitor 1 has the configuration of the above-described embodiment or each modification, the bag-shaped structure 32 can provide high blood pressure measurement accuracy and provide the cuff 12 of the blood pressure monitor 1 with an appropriate function, even when the cuff width is reduced.

The invention claimed is:

1. A bag-shaped structure used in a cuff for blood pressure measurement configured to be wrapped around a living body, inflate when a fluid is supplied to an internal space, and compress the living body, the bag-shaped structure comprising:

an inner wall portion provided on a living body side;
an outer wall portion facing the inner wall portion;
a pair of side wall portions, each being continuous with the inner wall portion and the outer wall portion and comprised of two portions joined to form a bent portion at the joint, bent toward the internal space; and
a reinforcing member provided on an outer surface of the pair of side wall portions on the bent portion of each of the pair of side wall portions, having a higher hardness than either of the pair of side wall portions, and having shape followability in a direction of wrapping around the living body.

2. The bag-shaped structure according to claim 1, wherein the reinforcing member includes a plurality of plate-shaped pieces provided at predetermined intervals in a longitudinal direction along each of the pair of side wall portions.

3. The bag-shaped structure according to claim 1, wherein the reinforcing member is provided along the longitudinal direction of the pair of side wall portions and is meshed.

4. The bag-shaped structure according to claim 1, wherein the bag-shaped structure comprises a plurality of the reinforcing members, the reinforcing members being provided at predetermined intervals in a longitudinal direction along each of the pair of side wall portions and each including a perforation on the bent portion along the bent portion.

5. The bag-shaped structure according to claim 1, wherein the inner wall portion and both of the pair of side wall portions have a Shore A hardness in a range from 15 to 95.

6. A bag-shaped structure used in a cuff for blood pressure measurement configured to be wrapped around a living body, inflate when a fluid is supplied to an internal space, and compress the living body, the bag-shaped structure comprising:

an inner wall portion provided on a living body side;
an outer wall portion facing the inner wall portion;
a pair of side wall portions, each being continuous with the inner wall portion and the outer wall portion and comprised of two portions joined to form a bent portion at the joint, bent toward the internal space;
a reinforcing member provided on an outer surface of the pair of side wall portions on the bent portion of each of the pair of side wall portions, having a higher hardness than either of the pair of side wall portions, and having shape followability in a direction of wrapping around the living body;
wherein the reinforcing member continues along each of an inner wall portion side and an outer wall portion side with respect to the bent portion; and
wherein the reinforcing member is provided along the longitudinal direction of the pair of side wall portions and is meshed.

7. A bag-shaped structure used in a cuff for blood pressure measurement configured to be wrapped around a living body, inflate when a fluid is supplied to an internal space, and compress the living body, the bag-shaped structure comprising:

an inner wall portion provided on a living body side;
an outer wall portion facing the inner wall portion;
a pair of side wall portions, each being continuous with the inner wall portion and the outer wall portion and comprised of two portions joined to form a bent portion at the joint, bent toward the internal space; and
a reinforcing member provided on an outer surface of each of the pair of side wall portions, having a higher hardness than either of the pair of side wall portions, and having shape followability in a direction of wrapping around the living body;

wherein the bag-shaped structure comprises a plurality of the reinforcing members, the reinforcing members being provided at predetermined intervals in a longitudinal direction along each of the pair of side wall portions and each including a perforation on the bent portion along the bent portion.

* * * * *